United States Patent
Luo et al.

(10) Patent No.: US 11,842,794 B2
(45) Date of Patent: Dec. 12, 2023

(54) VARIANT CALLING IN SINGLE MOLECULE SEQUENCING USING A CONVOLUTIONAL NEURAL NETWORK

(71) Applicant: The University of Hong Kong, Hong Kong (HK)

(72) Inventors: Ruibang Luo, Hong Kong (HK); Tak-Wah Lam, Hong Kong (HK); Chi-Man Liu, Hong Kong (HK)

(73) Assignee: THE UNIVERSITY OF HONG KONG, Hong Kong (HK)

( * ) Notice: Subject to any disclaimer, the term of this patent is extended or adjusted under 35 U.S.C. 154(b) by 956 days.

(21) Appl. No.: 16/358,662

(22) Filed: Mar. 19, 2019

(65) Prior Publication Data
US 2020/0303038 A1    Sep. 24, 2020

(51) Int. Cl.
*G16B 30/00* (2019.01)
*G06N 3/08* (2023.01)
*G16B 40/00* (2019.01)

(52) U.S. Cl.
CPC .............. *G16B 30/00* (2019.02); *G06N 3/08* (2013.01); *G16B 40/00* (2019.02)

(58) Field of Classification Search
CPC ........ G16B 30/00; G16B 40/00; G16B 40/20; G16B 20/20; G06N 3/02; G06N 20/00; G06N 3/08
(Continued)

(56) References Cited

U.S. PATENT DOCUMENTS
2018/0276333 A1    9/2018  Njie et al.

FOREIGN PATENT DOCUMENTS
CA    2894317 A1    12/2016
CA    3024017 A1    11/2017
(Continued)

OTHER PUBLICATIONS

Poplin, R., Chang, PC., Alexander, D. et al. A universal SNP and small-indel variant caller using deep neural networks. Nat Biotechnol 36, 983-987 (2018). (Year: 2018).*
(Continued)

*Primary Examiner* — Larry D Riggs, II
*Assistant Examiner* — Guozhen Liu
(74) *Attorney, Agent, or Firm* — Franklin & Associates International Inc; Matthew F. Lambrinos

(57) ABSTRACT

Systems and methods for variant calling in single molecule sequencing from a genomic dataset using a convolutional deep neural network. The method includes: transforming properties of each of the variants into a multi-dimensional tensor; passing the multi-dimensional tensors through a trained convolutional deep neural network to predict categorical output variables, the convolutional deep neural network minimizing a cost function iterated over each variant, the convolutional deep neural network trained using a training genomic dataset including previously identified variants, the convolutional neural network including: a plurality of pooled convolutional layers and at least two fully-connected layers connected sequentially after the last of the pooled convolutional layers, the at least two fully-connected layers comprising a second fully-connected layer connected sequentially after a first fully-connected layer; and outputting the predicted categorical output variables. In some cases, the categorical output variables include an alternate base, zygosity, variant type, and length of an indel.

9 Claims, 9 Drawing Sheets

Specification includes a Sequence Listing.

(58) Field of Classification Search
USPC .......................................................... 702/20
See application file for complete search history.

(56) References Cited

FOREIGN PATENT DOCUMENTS

| CN | 107609351 A1 | 1/2018 |
|---|---|---|
| WO | WO2017190211 A1 | 1/2017 |
| WO | WO2018165762 A1 | 9/2018 |

OTHER PUBLICATIONS

S. Albawi, T. A. Mohammed and S. Al-Zawi, "Understanding of a convolutional neural network," 2017 International Conference on Engineering and Technology (ICET), 2017, pp. 1-6, doi: 10.1109/ICEngTechnol.2017.8308186. (Year: 2017).*
Luo, R., Sedlazeck, F.J., Lam, TW. et al. A multi-task convolutional deep neural network for variant calling in single molecule sequencing. Nat Commun 10, 998 (2019). (Year: 2019).*
R Luo, FJ Sedlazeck, TW Lam, MC Schatz, Clairvoyante: a multi-task convolutional deep neural network for variant calling in single molecule sequencing.—bioRxiv, 2018—biorxiv.org. Posted Sep. 26, 2018. (Year: 2018).*
Sebastian Ruder: An Overview of Multi-Task Learning in Deep Neural Networks, arXiv:1706.05098 [cs.LG], Jun. 15, 2017 (Year: 2017).*
Zhang, XJ., Lu, YF. & Zhang, SH. Multi-Task Learning for Food Identification and Analysis with Deep Convolutional Neural Networks. J. Comput. Sci. Technol. 31, 489-500 (2016). https://doi.org/10.1007/s11390-016-1642-6 (Year: 2016).*
Philip Bachman, Ouais Alsharif, Doina Precup. Learning with Pseudo-Ensembles. Neural Information Processing Systems, Dec. 8-11, 2014, Montreal, Canada (Year: 2014).*
Petr Danecek, et. al, 1000 Genomes Project Analysis Group, The variant call format and VCFtools, Bioinformatics, vol. 27, Issue 15, Aug. 1, 2011, pp. 2156-2158 (Year: 2011).*
Skyhawk: An Artificial Neural Network-based discriminator for reviewing clinically significant genomic variants bioRxiv.
Katsanis SH, Katsanis N: Molecular genetic testing and the future of clinical genomics. Nat Rev Genet 2013, 14:415-426.
Zook JM, Catoe D, McDaniel J, Vang L, Spies N, Sidow A, Weng Z, Liu Y, Mason CE, Alexander N, et al: Extensive sequencing of seven human genomes to characterize benchmark reference materials. Sci Data 2016, 3:160025.
Robinson JT, Thorvaldsdottir H, Wenger AM, Zehir A, Mesirov JP: Variant Review with the Integrative Genomics Viewer. Cancer Res 2017, 77:e31-e34.
Woste M, Dugas M: VIPER: a web application for rapid expert review of variant calls. Bioinformatics 2018.
Uzilov AV, Ding W, Fink MY, Antipin Y, Brohl AS, Davis C, Lau CY, Pandya C, Shah H, Kasai Y: Development and clinical application of an integrative genomic approach to personalized cancer therapy. Genome medicine 2016, 8:62.
Luo R, Sedlazeck FJ, Lam T-W, Schatz M: Clairvoyante: a multi-task convolutional deep neural network for variant calling in Single Molecule Sequencing. bioRxiv 2018.
O'Rawe J, Jiang T, Sun G, Wu Y, Wang W, Hu J, Bodily P, Tian L, Hakonarson H, Johnson WE: Low concordance of multiple variant-calling pipelines: practical implications for exome and genome sequencing. Genome medicine 2013, 5:28. 8.
Van der Auwera GA, Carneiro MO, Hartl C, Poplin R, Del Angel G, Levy-Moonshine A, Jordan T, Shakir K, Roazen D, Thibault J, et al: From FastQ data to high confidence variant calls: the Genome Analysis Toolkit best practices pipeline. Curr Protoc Bioinformatics 2013, 43:11 10 11-33.
Luo R, Schatz MC, Salzberg SL: 16GT: a fast and sensitive variant caller using a 16-genotype probabilistic model. GigaScience 2017, 6:1-4.

Rehm HL, Bale SJ, Bayrak-Toydemir P, Berg JS, Brown KK, Deignan JL, Friez MJ, Funke BH, Hegde MR, Lyon E: ACMG clinical laboratory standards for nextgeneration sequencing. Genetics in medicine 2013, 15:733.
Hoffman-Andrews L: The known unknown: the challenges of genetic variants of uncertain significance in clinical practice. Journal of Law and the Biosciences 2017, 4:648.
Ng SB, Turner EH, Robertson PD, Flygare SD, Bigham AW, Lee C, Shaffer T, Wong M, Bhattacharjee A, Eichler EE: Targeted capture and massively parallel sequencing of 12 human exomes. Nature 2009, 461:272.
Goodwin, S., McPherson, J. D. & McCombie, W. R. Coming of age: ten years of next-generation sequencing technologies. Nat. Rev. Genet. 17, 333-351 (2016).
Nakamura, K. et al. Sequence-specific error profile of Illumina sequencers. Nucleic Acids Res. 39, e90 (2011).
Hatem, A., Bozdag, D., Toland, A. E. & Catalyurek, U. V. Benchmarking short sequence mapping tools. BMC Bioinforma. 14, 184 (2013).
Li, H. Toward better understanding of artifacts in variant calling from high-coverage samples. Bioinformatics 30, 2843-2851 (2014).
Luo, R., Schatz, M. C. & Salzberg, S. L. 16GT: a fast and sensitive variant caller using a 16-genotype probabilistic model. Gigascience 6, 1-4 (2017).
Van der Auwera, G. A. et al. From FastQ data to high confidence variant calls: the Genome Analysis Toolkit best practices pipeline. Curr. Protoc. Bioinforma. 43, 11 10 11-11 10 33 (2013).
Sedlazeck, F. J., Lee, H., Darby, C. A. & Schatz, M. C. Piercing the dark matter: bioinformatics of long-range sequencing and mapping. Nat. Rev. Genet.
Szegedy, C., Vanhoucke, V., Ioffe, S., Shlens, J. & Wojna, Z. Rethinking the inception architecture for computer vision. In Proceedings of the IEEE Conference on Computer Vision and Pattern Recognition. 2818-2826 (2016).
Consortium, G. P. A map of human genome variation from population-scale sequencing. Nature 467, 1061 (2010).
Loman, N. J., Quick, J. & Simpson, J. T. A complete bacterial genome assembled de novo using only nanopore sequencing data. Nat. Methods 12, 733 (2015).
Wilm, A. et al. LoFreq: a sequence-quality aware, ultra-sensitive variant caller for uncovering cell-population heterogeneity from high-throughput sequencing datasets. Nucleic Acids Res. 40, 11189-11201 (2012).
Leija-Salazar, M. et al. Detection of GBA missense mutations and other variants using the Oxford Nanopore MinION. bioRxiv, 288068 (2018.
Cleary, J. G. et al. Joint variant and de novo mutation identification on pedigrees from high-throughput sequencing data. J. Comput. Biol. 21, 405-419 (2014).
Zook, J. M. et al. Extensive sequencing of seven human genomes to characterize benchmark reference materials. Sci. Data 3, 160025 (2016).
Sandmann, S. et al. Evaluating variant calling tools for non-matched next-generation sequencing data. Sci. Rep. 7, 43169 (2017).
Lai, Z. et al. VarDict: a novel and versatile variant caller for next-generation sequencing in cancer research. Nucleic Acids Res. 44, e108-e108 (2016).
Garrison, E. & Marth, G.. Haplotype-based variant detection from short-read 728 sequencing. arXiv Preprint arXiv 1207.3907 (2012).
Li, H. Improving SNP discovery by base alignment quality. Bioinformatics 27, 1157-1158 (2011).
Li, H. et al. A synthetic-diploid benchmark for accurate variant-calling evaluation. Nat. Methods 15, 595 (2018).
Robinson, J. T., Thorvaldsdottir, H., Wenger, A. M., Zehir, A. & Mesirov, J. P. Variant Review with the Integrative Genomics Viewer. Cancer Res. 77, e31-e34 (2017).
Lu, H., Giordano, F. & Ning, Z. Oxford Nanopore MinION sequencing and genome assembly. Genom. Proteom. Bioinforma. 14, 265-279 (2016).
Zook, J. M. et al. Integrating human sequence data sets provides a resource of benchmark SNP and indel genotype calls. Nat. Biotechnol. 32, 246-251 (2014).

(56) References Cited

OTHER PUBLICATIONS

Sedlazeck, F. et al. Accurate detection of complex structural variations using single-molecule sequencing. Nat. Methods 15, 461-468 (2018).

Jain, M. et al. Nanopore sequencing and assembly of a human genome with ultra-long reads. Nat. Biotechnol. 36, 338-345 (2018).

Chin, J. Simple Convolutional Neural Network for Genomic Variant Calling with TensorFlow, https://towardsdatascience.com/simple-convolution-neural-network-for-genomic-variant-calling-with-tensorflow-c085dbc2026f (2017).

Abadi, M. et al. Tensorflow: Large-scale machine learning on heterogeneous distributed systems. arXiv preprint arXiv:1603.04467 (2016).

He, K., Zhang, X., Ren, S. & Sun, J. Delving deep into rectifiers: Surpassing human-level performance on imagenet classification. in Proceedings of the 2015 IEEE International Conference on Computer Vision (ICCV) 1026-1034 (IEEE Computer Society, 2015).

Klambauer, G., Unterthiner, T., Mayr, A. & Hochreiter, S. Self-Normalizing Neural Networks. arXiv preprint arXiv:1706.02515 (2017).

Kingma, D. & Ba, J. Adam: A method for stochastic optimization. arXiv preprint arXiv:1412.6980 (2014).

Hinton, G. E., Srivastava, N., Krizhevsky, A., Sutskever, I. & Salakhutdinov, R. R. Improving neural networks by preventing co-adaptation of feature detectors. arXiv preprint arXiv:1207.0580 (2012).

Cortes, C., Mohri, M. & Rostamizadeh, A. June. L 2 regularization for learning kernels. in Proceedings of the Twenty-Fifth Conference on Uncertainty in Artificial Intelligence. 109-116 (AUAI Press, 2009).

Alted, F. Blosc: A Blocking, Shuffling and Lossless Compression Library http://blosc.org/ (2018).

\* cited by examiner

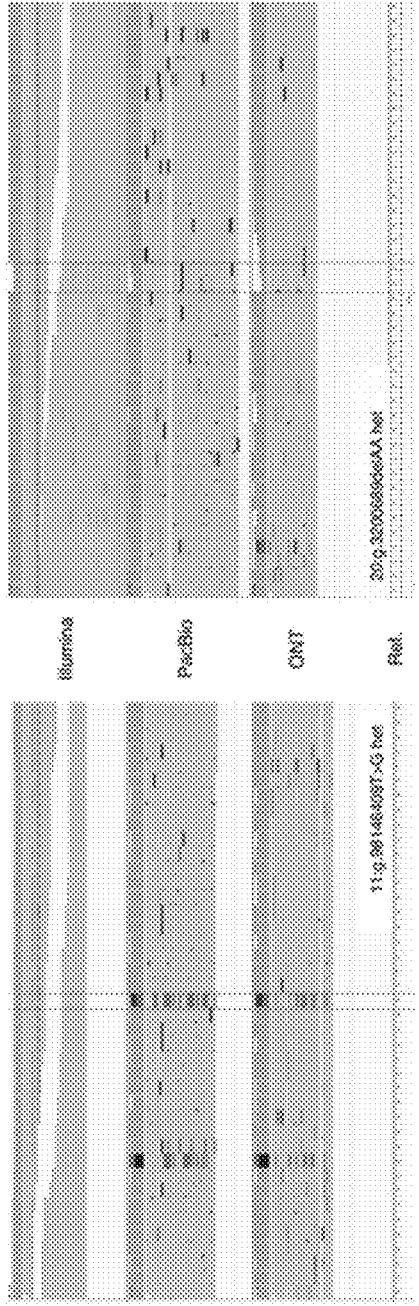
FIG. 5A
FIG. 5B
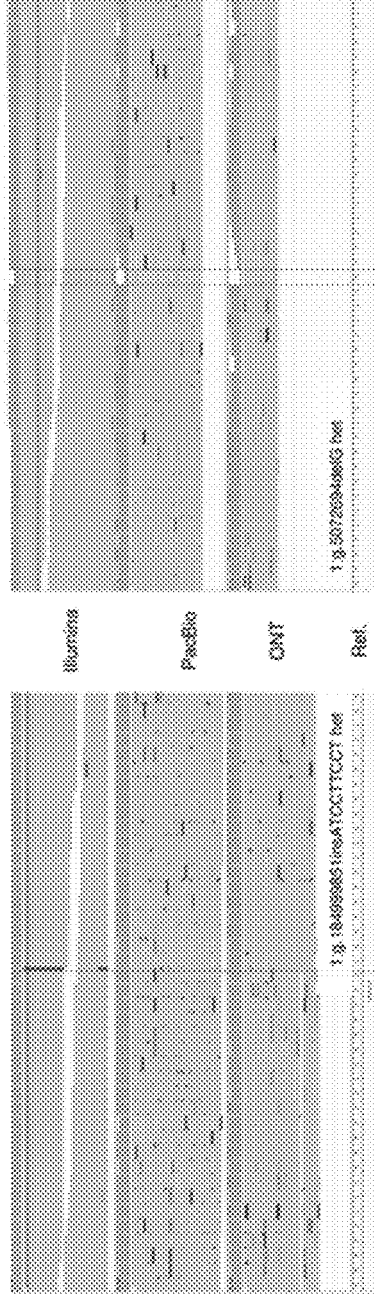
FIG. 5C
FIG. 5D

VARIANT CALLING IN SINGLE MOLECULE SEQUENCING USING A CONVOLUTIONAL NEURAL NETWORK

TECHNICAL FIELD

The following relates generally to artificial neural networks and more specifically to a system and method for variant calling in single molecule sequencing using a convolutional neural network.

SEQUENCE LISTING

The following application contains a sequence listing submitted as a text file in ASCII format, the name of the ASCII text file being PA02069NPascii_ST25, the date of creation of the ASCII text file being Oct. 25, 2019, and the size of the ASCII text file being 2 KB. The content of the ASCII text is hereby incorporated by reference.

BACKGROUND

The accurate identification of DNA sequence variants is an important, but challenging task in genomics. It is particularly difficult for single molecule sequencing, which has a per-nucleotide error rate of approximately 5% to 15%. It is necessary to accurately and efficiently determine variants so that the genomic variants that underlie phenotypic differences and disease can be correctly detected. However, the sequences upon which variation can be examined is often limited.

SUMMARY

In an aspect, there is provided a computer-implemented method for variant calling in single molecule sequencing from a genomic dataset using a convolutional deep neural network, the method comprising: obtaining variants of the genomic dataset; transforming properties of each of the variants into a multi-dimensional tensor; passing the multi-dimensional tensors through a trained convolutional deep neural network to predict categorical output variables, the convolutional deep neural network minimizing a cost function iterated over each variant, the convolutional deep neural network trained using a training genomic dataset comprising previously identified variants, the convolutional neural network comprising: an input layer; a plurality of pooled convolutional layers connected sequentially after the input layer, each pooled convolutional layer taking an input, applying at least one convolutional operation to the input, and applying a pooling operation to the output of the convolutional operation; and at least two fully-connected layers connected sequentially after the last of the pooled convolutional layers, the at least two fully-connected layers comprising a second fully-connected layer connected sequentially after a first fully-connected layer; and outputting the predicted categorical output variables.

In a particular case, for each variant, the categorical output variables comprise: a first categorical output variable comprising an alternate base at a single-nucleotide polymorphism; a second categorical output variable comprising zygosity; a third categorical output variable comprising type; and a fourth categorical output variable comprising length of an insertion or deletion of bases.

In another case, the first categorical output variable is selected from a group comprising adenine (A), cytosine (C), guanine (G), and thymine (T), the second categorical output variable is selected from a group comprising Homozygote and Heterozygote, the third categorical output variable is selected from a group comprising Reference, SNP, Insertion, and Deletion, and the fourth categorical output variable is selected from a group comprising 0, 1, 2, 3, 4, and greater than 4.

In yet another case, the first categorical output variable is output from the first fully-connected layer, and the second categorical output variable, the third categorical output variable, and the fourth categorical output variable are outputted from the second fully-connected layer.

In yet another case, the first fully-connected layer comprises a regression analysis using a sigmoid activation function, and the second fully-connected layer comprises a softmax classification analysis.

In yet another case, the plurality of pooled convolutional layers comprises exactly three pooled convolutional layers.

In yet another case, the multi-dimensional tensor comprises a first dimension corresponding to a position of the variant in addition to flanking base pairs, a second dimension corresponding to a count of a base on a sequencing read, and a third dimension corresponding to a number of techniques for counting bases.

In yet another case, the first dimension comprises sixteen flanking base pairs on both sides of the variant for a total dimension of thirty-three, the second dimension comprises adenine (A), cytosine (C), guanine (G), and thymine (T) for a total dimension of four, and the third dimension comprises four techniques for counting bases for a total dimension of four.

In yet another case, the four techniques comprise a first technique for encoding a reference sequence and a number of reads supporting reference alleles, and the second technique encodes inserted sequences, the third technique encodes deleted base-pairs, and the fourth technique encodes alternative alleles.

In another aspect, there is provided a system for variant calling in single molecule sequencing from a genomic dataset using a convolutional deep neural network, the system comprising one or more processors and one or more non-transitory computer storage media, the one or more non-transitory computer storage media causing the one or more processors to execute: an input module to obtain variants of the genomic dataset and transform properties of each of the variants into a multi-dimensional tensor; a machine learning module to pass the multi-dimensional tensors through a trained convolutional deep neural network to predict categorical output variables, the convolutional deep neural network minimizing a cost function iterated over each variant, the convolutional deep neural network trained using a training genomic dataset comprising previously identified variants, the convolutional neural network comprising: an input layer; a plurality of pooled convolutional layers connected sequentially after the input layer, each pooled convolutional layer taking an input, applying at least one convolutional operation to the input, and applying a pooling operation to the output of the convolutional operation; and at least two fully-connected layers connected sequentially after the last of the pooled convolutional layers, the at least two fully-connected layers comprising a second fully-connected layer connected sequentially after a first fully-connected layer; and an output module to output the predicted categorical output variables.

In a particular case, for each variant, the categorical output variables comprise: a first categorical output variable comprising an alternate base at a single-nucleotide polymorphism; a second categorical output variable comprising zygosity; a third categorical output variable comprising type; and a fourth categorical output variable comprising length of an insertion or deletion of bases.

In another case, the first categorical output variable is selected from a group comprising adenine (A), cytosine (C), guanine (G), and thymine (T), the second categorical output variable is selected from a group comprising Homozygote and Heterozygote, the third categorical output variable is selected from a group comprising Reference, SNP, Insertion, and Deletion, and the fourth categorical output variable is selected from a group comprising 0, 1, 2, 3, 4, and greater than 4.

In yet another case, the first categorical output variable is output from the first fully-connected layer, and the second categorical output variable, the third categorical output variable, and the fourth categorical output variable are outputted from the second fully-connected layer.

In yet another case, the first fully-connected layer comprises a regression analysis using a sigmoid activation function, and the second fully-connected layer comprises a softmax classification analysis.

In yet another case, the plurality of pooled convolutional layers comprises exactly three pooled convolutional layers.

In yet another case, the multi-dimensional tensor comprises a first dimension corresponding to a position of the variant in addition to flanking base pairs, a second dimension corresponding to a count of a base on a sequencing read, and a third dimension corresponding to a number of techniques for counting bases.

In yet another case, the first dimension comprises sixteen flanking base pairs on both sides of the variant for a total dimension of thirty-three, the second dimension comprises adenine (A), cytosine (C), guanine (G), and thymine (T) for a total dimension of four, and the third dimension comprises four techniques for counting bases for a total dimension of four.

In yet another case, the four techniques for counting bases comprise a first technique for encoding a reference sequence and a number of reads supporting reference alleles, and the second technique encodes inserted sequences, the third technique encodes deleted base-pairs, and the fourth technique encodes alternative alleles.

In another aspect, there is provided a computer-implemented method for validating variant calling from a genomic dataset received from a separate variant caller, the method comprising: obtaining variants of the genomic dataset; receiving candidate categorical output variables of the variants from the separate variant caller; transforming properties of each of the variants into a multi-dimensional tensor; passing the multi-dimensional tensors through a trained convolutional deep neural network to predict categorical output variables, the convolutional deep neural network minimizing a cost function iterated over each variant, the convolutional deep neural network trained using a training genomic dataset comprising categorical output variables of previously identified variants, the convolutional neural network comprising: an input layer; a plurality of pooled convolutional layers connected sequentially after the input layer, each pooled convolutional layer taking an input, applying at least one convolutional operation to the input, and applying a pooling operation to the output of the convolutional operation; and at least two fully-connected layers connected sequentially after the last of the pooled convolutional layers, the at least two fully-connected layers comprising a second fully-connected layer connected sequentially after a first fully-connected layer; and determining an output condition for each variant, the output condition comprising a positive condition if all categorical output variables for the variant match the candidate output variables for the variant, otherwise the output condition comprising a negative condition; outputting the output conditions.

In a particular case, the method further comprising determining and outputting a quality score, the quality score determination comprising determining a distance between a best prediction and a second-best prediction of the trained convolutional deep neural network for each variant.

These and other aspects are contemplated and described herein. It will be appreciated that the foregoing summary sets out representative aspects of a system and method for training a residual neural network and assists skilled readers in understanding the following detailed description.

DESCRIPTION OF THE DRAWINGS

A greater understanding of the embodiments will be had with reference to the Figures, in which:

FIG. 5A illustrates an example visualization of heterozygote SNP from T to G at chromosome 11, in accordance with the system of FIG. 1;

FIG. 5B illustrates an example visualization of heterozygote deletion AA at chromosome 20, in accordance with the system of FIG. 1;

FIG. 5C illustrates an example visualization of heterozygote insertion ATCCTTCCT at chromosome 1, in accordance with the system of FIG. 1;

FIG. 5D illustrates an example visualization of heterozygote deletion G at chromosome 1, in accordance with the system of FIG. 1;

DETAILED DESCRIPTION

Figure 1:
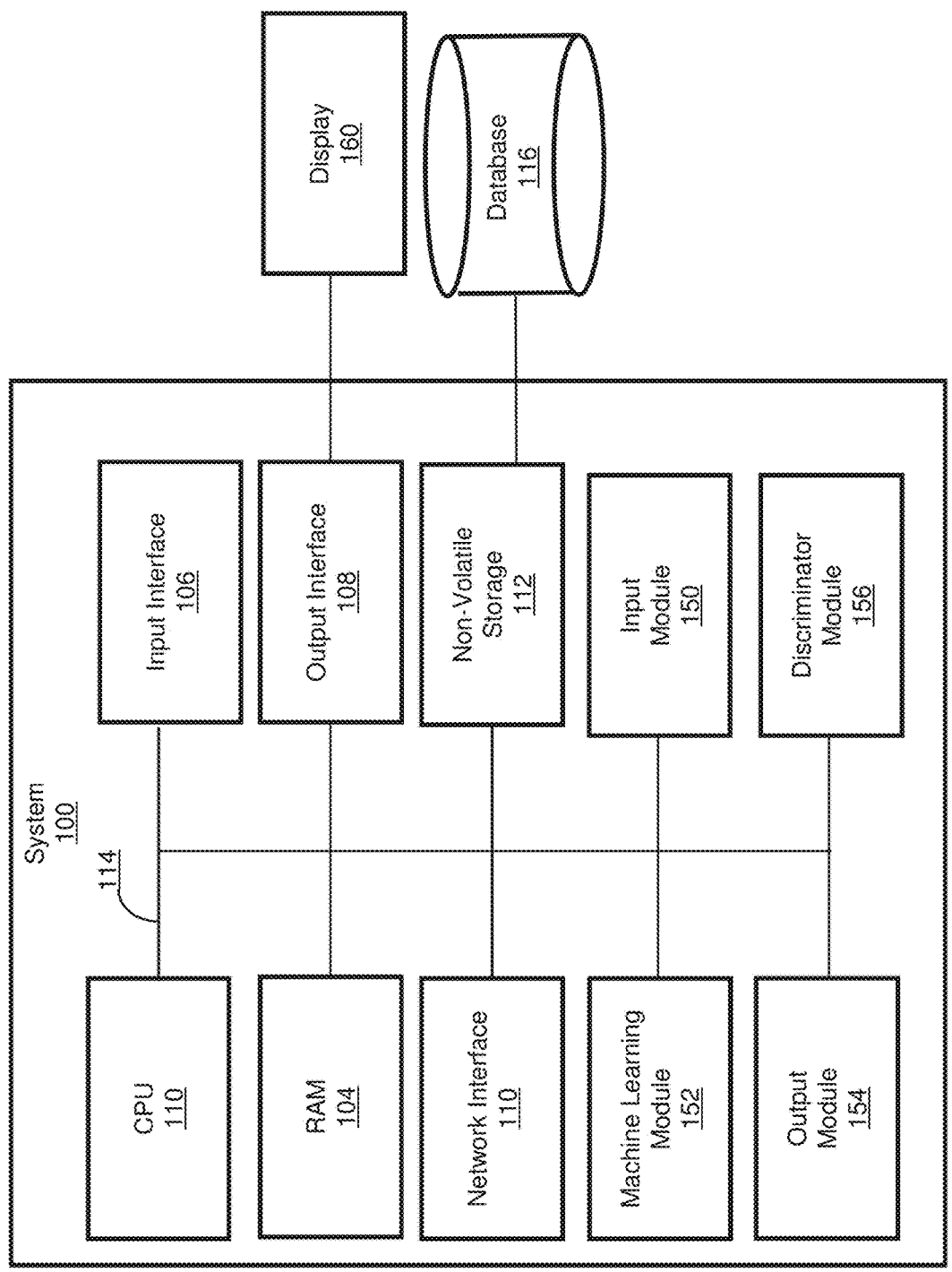
FIG. 1 is a schematic diagram of a system for variant calling in single molecule sequencing using a convolutional neural network, in accordance with an embodiment.

Embodiments will now be described with reference to the figures. For simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

Any module, unit, component, server, computer, terminal or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Any application or module herein described may be implemented using computer readable/executable instructions that may be stored or otherwise held by such computer readable media.

A fundamental problem in genomics is finding nucleotide differences in an individual genome relative to a reference sequence, often referred to as variant calling. It is generally ideal to accurately and efficiently call variants so that the genomic variants that underlie phenotypic differences and disease can be sufficiently detected. Different data characteristics may contribute to higher variant calling performance; for example, properties of the sequencing instrument, quality of preceding sequence aligners, and alignability of a genome reference. Variant calling pipelines may use these characteristics, however, most of these pipelines are only able to be used for short read sequencing.

Single Molecule Sequencing (SMS) approaches generate sequencing reads two orders of magnitude longer than standard short-read Illumina sequencing (10 kbp to 100 kbp instead of ~100 bp), but generally they also contain 5%-15% sequencing errors rather than ~1% for Illumina. Single nucleotide and small indel variant calling with SMS remains substantially challenging because various approaches for variant calling fail to handle such a high sequencing error rate, especially one enriched for indel errors. Advantageously, embodiments of the present disclosure provide, at least, single nucleotide and small indel variant calling with SMS that produce a substantially reduced error rate.

Artificial Neural Networks (ANNs) can be used for DNA variant detection by applying ANNs to analyzing images of aligned reads around candidate variants. While some approaches use image classifiers, doing so may be suboptimal for variant calling because valuable information that could contribute to higher accuracy are lost during the image transformation.

In the present embodiments, a convolutional deep neural network is provided for variant calling with SMS reads. Advantageously, the present embodiments can, for example, predict variant type (SNP or indel), zygosity, alternative allele, and indel length from aligned reads. The present inventors performed an example experiment that verified that the present embodiments can call variants in multiple human genomes both at common variant sites and genome-wide show are as accurate as approaches on Illumina data but with longer sequencing, and substantially more accurate and computationally efficient as other approaches on PacBio and ONT data.

While the present embodiments are generally described as targeting SMS, it is understood that the present embodiments can also be generally applicable to short read data.

FIG. 1 shows various physical and logical components of an embodiment of a system for variant calling in single molecule sequencing using a convolutional deep neural network 100. As shown, the system 100 has a number of physical and logical components, including a central processing unit ("CPU") 102 (comprising one or more processors), random access memory ("RAM") 104, an input interface 106, an output interface 108, a network interface 110, non-volatile storage 112, and a local bus 114 enabling the CPU 102 to communicate with the other components. The CPU 102 executes executable instructions for implementing the convolutional deep neural network, including various modules, as described below in greater detail. The CPU 102 can itself be, or can be used in conjunction with, a graphical processing unit (GPU). RAM 104 provides relatively responsive volatile storage to the CPU 102. The input interface 106 enables an administrator or user to provide input via an input device, for example a keyboard and mouse. The input interface 106 can be used to receive genomic data. In other cases, the genomic data can be located on the database 116 or received via the network interface 110. The output interface 108 outputs information to output devices, for example, a display 160 and/or speakers. The network interface 110 permits communication with other systems, such as other computing devices and servers remotely located from the system 100, such as for a typical cloud-based access model. Non-volatile storage 112 stores the operating instructions as well as data used by the system. Additional stored data can be stored in a database 116. During operation of the system 100, the instructions and data may be retrieved from the non-volatile storage 112 and placed in RAM 104 to facilitate execution. In this embodiment, the system 100 is run on a client side device and accesses content located on a server over a network, such as the internet. In further embodiments, the system 100 can be run on any other computing device; for example, a desktop computer, a laptop computer, a smartphone, a tablet computer, a server, a smartwatch, distributed or cloud computing device(s), or the like.

In an embodiment, the CPU 102 is configurable to execute an input module 150, a machine learning module 152, an output module 154, and a discriminator module 156. As described herein, the machine learning module 152 is able to build and use an embodiment of a deep convolutional neural network architecture.

In an embodiment, the system 100 can model a number of different types of genomic variant characteristics with categorical variables. In a particular case, at least one of four categorical variables can be used, including:

$A \in \{A, C, G, T\}$ is an alternate base at a single-nucleotide polymorphism (SNP), or the reference base otherwise;

$Z \in \{Homozygote, Heterozygote\}$ is a zygosity of a variant;

$T \in \{Reference, SNP, Insertion, Deletion\}$ is a variant type; and $L \in \{0, 1, 2, 3, 4, >4\}$ is a length of an insertion or deletion of bases (indel), where '>4' represents a gap longer than 4 base pairs (bp).

In some cases, all the A, Z, T, and L variables can be used. In further cases, any suitable subset of the A, Z, T, and L variables can be used. It is also understood that other suitable options for the variables can be used; for example L∈{0, 1, 2, 3, 4, 5, >5}. In the above embodiment, L∈{0, 1, 2, 3, 4, >4} was selected by the present inventors because, generally, Indels longer than 4 are rare (<1% among Indels of all sizes).

Training data is used to train the convolutional neural network, as described herein. The training data includes variants previously identified with values for all the A, Z, T, and L variables, or the subset of the A, Z, T, and L variables identified above. In some cases, each variable of the training data can be represented by a vector (for example, with a one-dimensional tensor) using one-hot or probability encoding. Whereby: $a_b = \Pr\{A=b\}$, $z_i = \delta(i, Z)$, $t_j = \delta(j, T)$ and $l_k = \delta(k, L)$, where $\delta(p, q)$ equals 1 if $p=q$, or 0 otherwise. The four vectors (a, z, t, l) are the outputs of the convolutional neural network. In some cases, $a_b$ is set to all zero for an insertion or deletion. In some cases, multi-allelic SNPs are excluded from training, and base-quality is not used.

In the present embodiment, the system 100 seeks a function F: $x \rightarrow (a, z, t, l)$ that minimizes the cost C:

$$C = \frac{1}{N} \sum_{v} \left( \sum_{b=1}^{4} (\hat{a}_b^{(v)} - a_b^{(v)})^2 - \sum_{i=1}^{2} z_i^{(v)} \log \hat{z}_i^{(v)} - \sum_{j=1}^{4} t_j^{(v)} \log \hat{t}_j^{(v)} - \sum_{k=1}^{6} l_k^{(v)} \log \hat{l}_k^{(v)} \right)$$

where v iterates through all variants and a variable with a caret indicates it is an estimate from the neural network. Variable x is the input of the network, and it can be of any suitable shape and contain any suitable information. This embodiment uses an x that contains a summarized "piled-up" representation of read alignments, as described herein.

Figure 3:
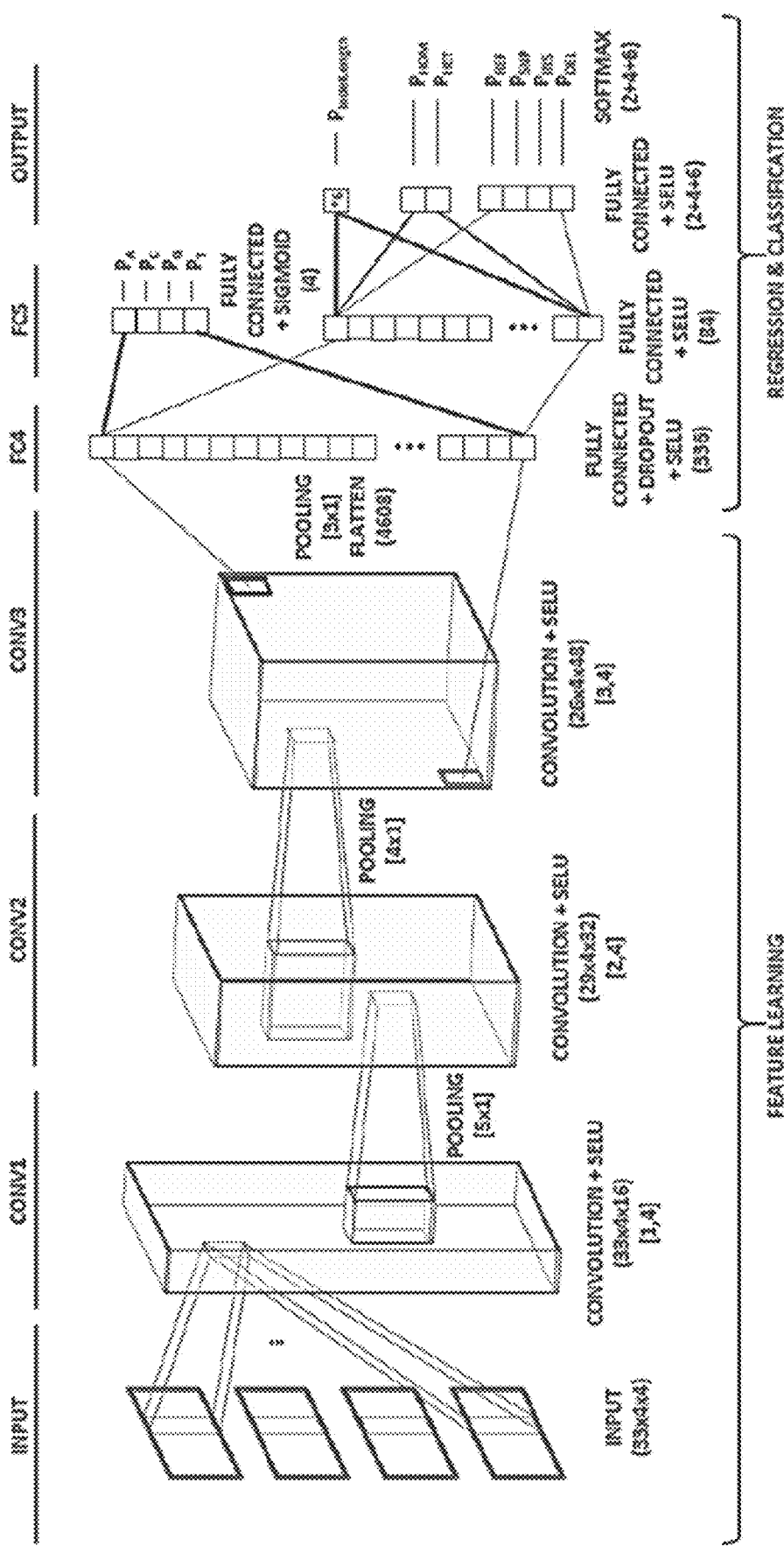
FIG. 3 is a diagram of an example neural network architecture for the system of FIG. 1.

Turning to FIG. 3, a diagrammatic example of the convolutional neural network, according to the present embodiments, is shown. In FIG. 3, the labels under each layer include 1) the layer's function; 2) the activation function used; 3) the dimension of the layer in parenthesis (Input layer: Height×Width×Arrays, Convolution layer: Height×Width×Filters, Fully connected layer: Nodes); and 4) kernel size in brackets (Height×Width). In this example, the convolutional neural network is a multi-task five-layer convolution neural network with the last two layers as feedforward layers. In this example, the neural network generates four groups of predictions on each input: 1) alternative alleles, 2) zygosity, 3) variant type, and 4) indel length. In this case, the predictions in groups 2, 3 and 4 are mutually exclusive while the predictions in group 1 are not. In this example, the alternative allele predictions can be determined directly from the first fully connected layer (FC4), while the other three group of predictions can be determined from the second fully connected layer (FC5). The indel length prediction group has six possible outputs indicating an indel with a length between 0 to 3 bp or greater than 4 bp of any unbounded length. In many cases, the prediction limit on indel length can be configurable and can be raised when more training data on longer indels is provided. Advantageously, the convolutional neural network as shown has been experimented with by the present inventors and found to be succinct and fine-tuned for the variant calling purpose. It contains only 1,631,496 parameters, about 13-times fewer than other approaches, for example, the DeepVariant approach using the Inception-v3 network architecture.

Through extensive and arduously laborious testing, involving at least hundreds of iterations of CNN architectures and combinations of hyperparameters, the present inventors arrived at the above CNN architecture exemplified in FIG. 3. This architecture was determined to best capture genomic features from sequence alignment for variant calling, as described herein. For example, this architecture achieved the best F1-score (the harmonic mean of precision and recall) on numerous test cases (those variants kept for performance testing and not training). During such testing, the CNN architectures were determined with hyperparameters having some general directions, for example, using three convolutional layers to reduce the dimension of input. According to the testing, three layers were approximately enough to generate abstracted features of the read alignments in input. According to the testing, this quantity of layers was able to achieve a good performance while also running sufficiently fast. The two fully connect layers were used to perform a non-linear regression on the abstracted features. In the testing, the number of nodes in the two fully connected layers were set to maximize the AUC (area under curve) on the test cases while not significantly increasing the computation time.

Advantageously, the multi-task architecture of the present embodiments is used to solve variant calling in just a single model, which was a substantial technical challenge in bioinformatics. As described herein, such architecture significantly increased the computational speed by, for example, using just a single model for all tasks. The multi-task architecture also increased the performance of the CNN architecture generally by lowering the chance of overfitting to a single task. Additionally, the present inventors identified the technical advantages of having the output variable A output by the first fully-connected layer, for example, from recognizing the diploid nature of human genomics whereby only two different bases or just a single base is possible; while the other three output variables, Z, T and L, can be output by the second fully-connected layer.

Figure 4:
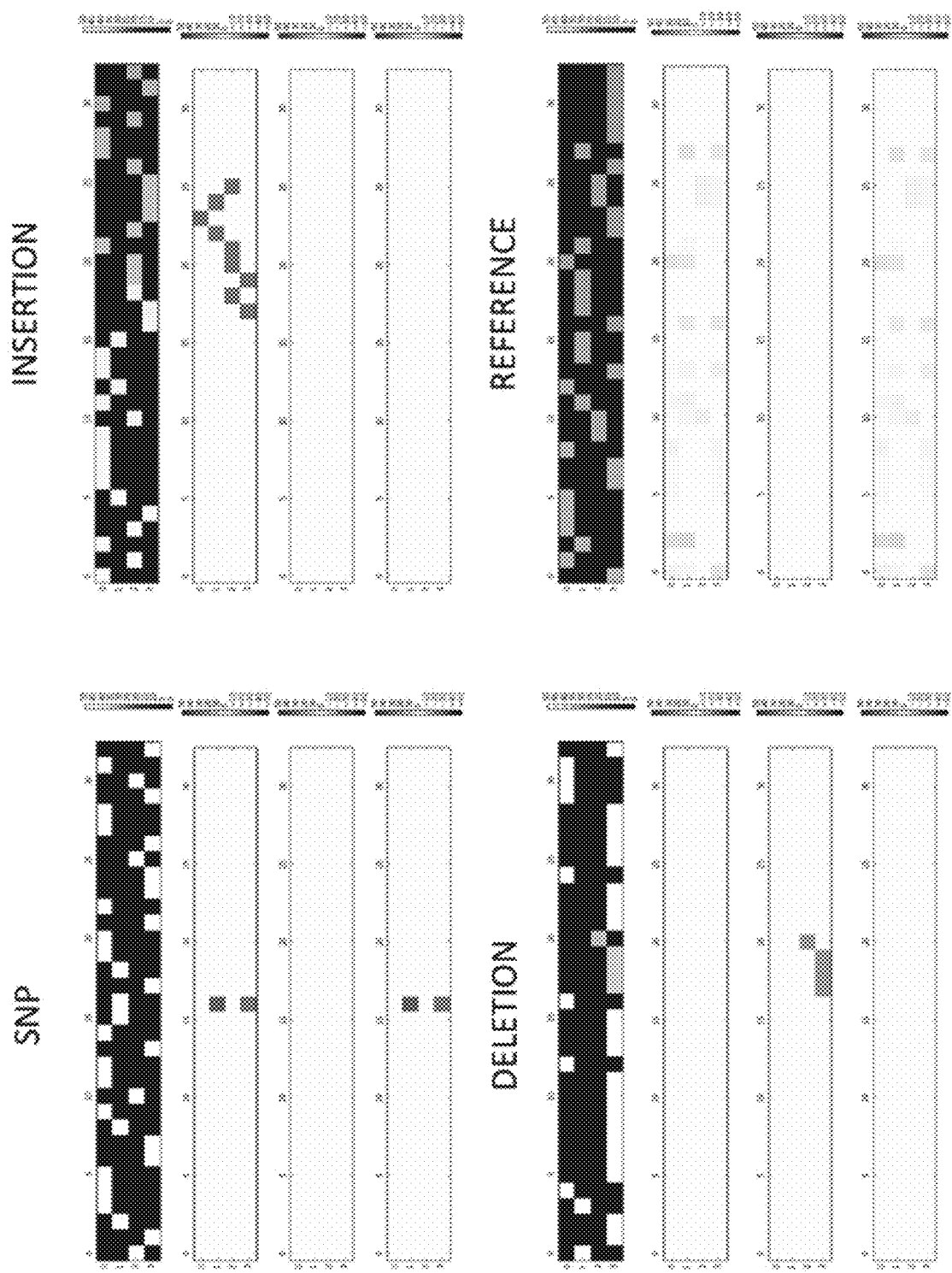
FIG. 4 shows representations of three types of small variants, and a non-variant, in accordance with the system of FIG. 1.

As shown in FIG. 3, in an embodiment, for each input sample, overlapping sequencing read alignments can be transformed into a multi-dimensional tensor x. In a particular case, the multi-dimensional tensor x can have a shape of 33 by 4 by 4. The first dimension '33' corresponds to the position of the variant. The second dimension '4' corresponds to the count of A, C, G, or T on the sequencing reads, where the method of counting is subject to the third dimension. The third dimension '4' corresponds to four different ways of counting. In this embodiment, for the first dimension, 16 flanking base-pairs were added to both sides of a candidate (for a total of 33 bp). The present inventors measured this dimension to be sufficient to manifest background noise while providing good computational efficiency. For the second dimension, counts were separated into four bases. For the third dimension, four different ways of counting were used, generating four tensors of shape 33 by 4. The first tensor encodes the reference sequence and the number of reads supporting the reference alleles. The second, third and fourth tensors use the relative count against the first tensor: the second tensor encodes the inserted sequences, the third tensor encodes the deleted base-pairs, and the fourth tensor encodes alternative alleles. FIG. 4 illustrates an example of how the tensors can represent a SNP, an insertion, a deletion, and a non-variant (reference), respectively. The non-variant in FIG. 4 also depicts an example of background noise. Advantageously, the convolutional neural network of the present embodiments decouples a substitution and insertion signal into separate arrays and allows for the precise recording of an allele of an inserted sequence.

In the above case, flanking bases can be used to provide localized background noise of the target variant. Bases to the right of a target variant can also be used to provide a "length" and "the exact inserted or deleted bases" if the variant is an Indel.

Additionally, the present architecture separates the count of bases (A, C, G, T) in the input samples from the ways of counting a single, 1) reference, 2) a deletion, 3) an insertion, and 4) a SNP, such that they are in separate channels. Advantageously, this can facilitate the CNN architecture to better make use of the count of different singles; for example, the network does not need to tease out the singles of different variant types itself.

Figure 9:
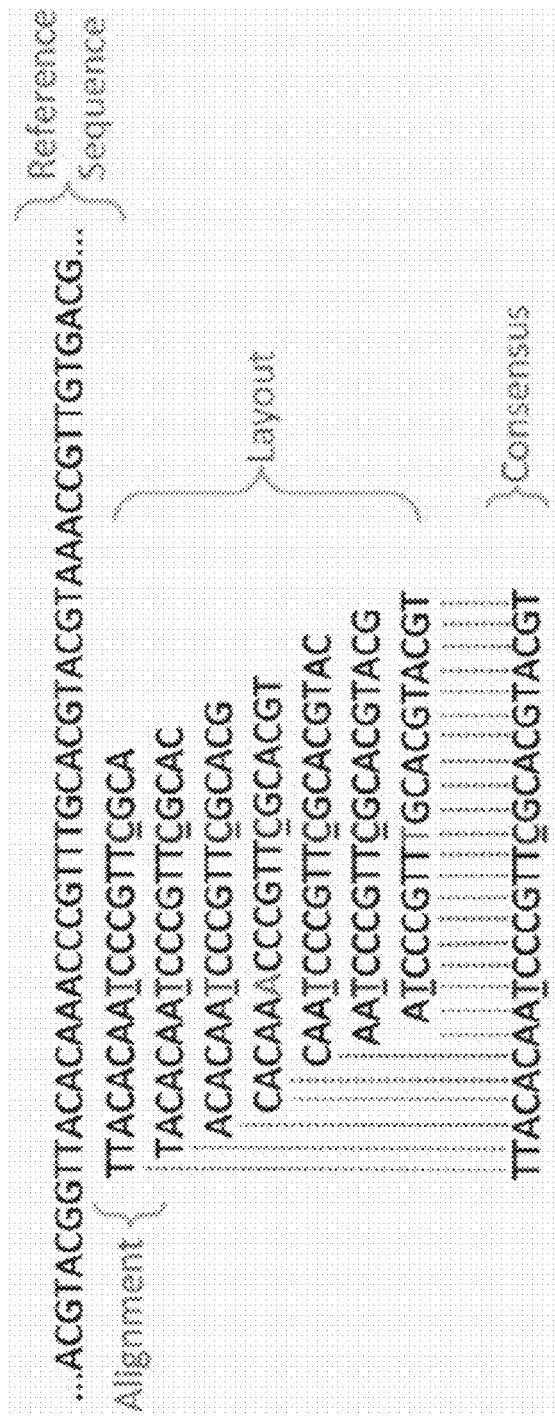
FIG. 9 illustrates an example of counting A, C, G, or T on the sequencing reads.

Turning to FIG. 9, an example of counting A, C, G, or T on the sequencing reads is illustrated. The first row is a reference DNA sequence and the strings in the middle are sequencing reads. Generally, the starting position of a sequencing read is its alignment and a collection of alignments is a layout. For each position in the reference sequence, the layout provides the count of bases A, C, G, T of the sequencing reads at that position. The underlined bases suggest a variant at a reference position because the base with majority count is different from the reference base. The bases that are highlighted but not underlined are possible sequencing errors.

In an example for illustration purposes, the following pseudocode can be used to generate the input sample:

```
Input: p, genome position of a candidate variant, 1 -based
    r, reference genome
    a, a set of elements representing the read alignments covering p at bp
    level, each element contains four members:
        1) the matched reference position (refpos), 1-based,
        2) the offset of this bp within its insertion pattern (insoffset), 1-
        based (only applicable if this bp is an inserted base),
        3) the bp 'A' or 'C' or 'G' or 'T' or the gap '—' in r at refpos
        (refbase),
        4) the bp or the gap in the corresponding aligned read at
        readpos (readbase).
Output: A matrix x of order 33 by 4 by 4
h.insert('A', 0)
h.insert('C', 1)
h.insert('G', 2)
h.insert('T', 3)
create a zero-filled matrix x of size (33 x 4 x 4)
for each item in a do:
    /* Skip the Ns and IUPAC nucleotides in reference */
    if a[item].refbase not one of "ACGT-" then:
        continue
    /* Skip the Ns in read */
    if a[item].readbase not one of "ACGT-" then:
        continue
    /* Center the candidate variant in the first dimension (33) of x */
    offset <- refpos – p + 16
    /* Skip if beyond scope */
    if offset < 0 or offset > 32 then:
        continue
    /* Translate refbase and readbase into index */
    refbaseIndex <- h.get(a[item].refbase)
    readbaseindex <- h.get(a[item].readbase)
    /* If not a deleted base */
    if a[item].readbase ≠ '—' then:
        /* If not an inserted base either, i.e. a ref or a SNP */
        if a[item].refbase ≠ '—' then:
            increase x[offset][refbaseIndex][0] by 1
            increase x[offset][readbaseIndex][1] by 1
            increase x[offset][refbaseIndex][2] by 1
            increase x[offset][readbaseIndex][3] by 1
        /* If is a inserted base */
        if a[item].refbase = '—' then:
            newOffset <- min(offset + a[item].insoffset, 32)
            increase x[newOffset][readbaseIndex][1] by 1
    /* If is a deleted base */
    if a[item].readbase = '—' then:
        increase x[offset][refbaseIndex][2] by 1
```

```
for i = 0 to 32 do:
    for j = 0 to 3 do:
        x[i][j][1] <- x[i][j][0]
        x[i][j][2] <- x[i][j][2] – x[i][j][0]
        x[i][j][3] <- x[i][j][3] – x[i][j][0]
return x
```

FIG. 4 shows selected illustrations of how the present embodiments represent three common types of small variants, and a non-variant. Each variant is presented with counts A, C, G, or T, top to bottom respectively. A C>G SNP in the top-left illustration, a 9 bp insertion in the top-right illustration, a 4 bp deletion in the bottom-left illustration, and a non-variant with reference allele in the in the bottom-right illustration. The intensity represents the strength of a certain variant signal. The SNP, insertion and deletion examples are ideal with almost zero background noise. The non-variant example illustrates how the background noises look like when not mingled with any variant signal.

During training of the convolutional neural network, the system 100 can perform weight initialization to stabilize the variances of activation and back-propagated gradients at the beginning of model training. In some cases, a He initializer can be used to initialize the weights of hidden layers in the convolutional neural network because the He initializer is generally optimized for training extremely deep models using rectified activation functions directly from scratch. In these cases, for each layer, the weight of each node can be sampled from a univariate normal distribution with $\sigma = 1 \div \sqrt{d_i \pm 2}$, where $d_i$ denotes the number of in-degree of the node. In further cases, other suitable weight initialization approaches can be used.

In some embodiments, the system 100 can use batch normalization to ensure zero mean and unit variance in each hidden layer of the convolutional neural network; such that exploding or diminishing gradients can be avoided during training. In some cases, batch normalization can be a computational bottleneck in neural network training because computing the mean and the standard deviation of a layer is not only a dependent step, but also a reduction step that cannot be efficiently parallelized. Accordingly, in some embodiments, the system 100 can use "Scaled Exponential Linear Units" (SELUs), which is a variant of a rectified activation function, as an activation function. Different from a standard batch normalization approach that adds an implicit layer for the named purpose after each hidden layer, SELUs utilize a Banach fixed-point theorem to ensure convergence to zero mean and unit variance in each hidden layer without batch normalization.

In some embodiments, the system 100 can use an Adam optimizer to update the weights of the convolutional neural network by adaptive node-specific learning rates. In this case, setting a global learning rate functions as setting an upper limit to the learning rates. This approach advantageously allows the system 100 to remain at a higher learning rate for a longer time to speed up the training process. In some cases, while the Adam optimizer performs learning rate decay intrinsically, the system 100 can decrease the global learning rate when the cost of the model in training plateaued can lead to a better model performance. For example, in some cases, there may be two types of training modes. A fast training mode can use an adaptive decay method that uses an initial learning rate at, for example, $1e^{-3}$ and decreases the learning rate by a factor of, for example, 0.1 when the validation rate goes up and down for five rounds and stops after two times of decay. A nonstop training mode can receive a user's input as to when to stop and continue using a lower learning rate.

In some embodiments, even though there may be many labeled truth variants in the training set, the scarcity of some labels, for example variants with a long indel length, could fail the model training by overfitting to abundantly labeled data. To address the class imbalance, dropout and/or L2 regularization can be applied by the system 100. During training, dropout can be used to randomly ignore nodes in a layer with probability p, then sum up the activations of remaining nodes, and finally magnify the sum by 1/p. Then during testing, the activations of all nodes can be summed with no dropout. With probability p, the dropout technique is effectively creating up to $1 \div (1-p)^n$ possible subnetworks during the training. Therefore, dropout can be seen as dividing a network into subnetworks with reused nodes during training. However, in some cases, for a layer with just enough nodes available, applying dropout may require more nodes to be added, thus potentially increasing the time needed to train a model. In an embodiment, dropout can be applied only to the first fully connected layer (FC4) with p=0.5, and L2 regularization can be applied to the hidden layers of the convolutional neural network. In some cases, the system 100 can set the lambda of L2 regularization to be the same as the learning rate.

Figure 2:
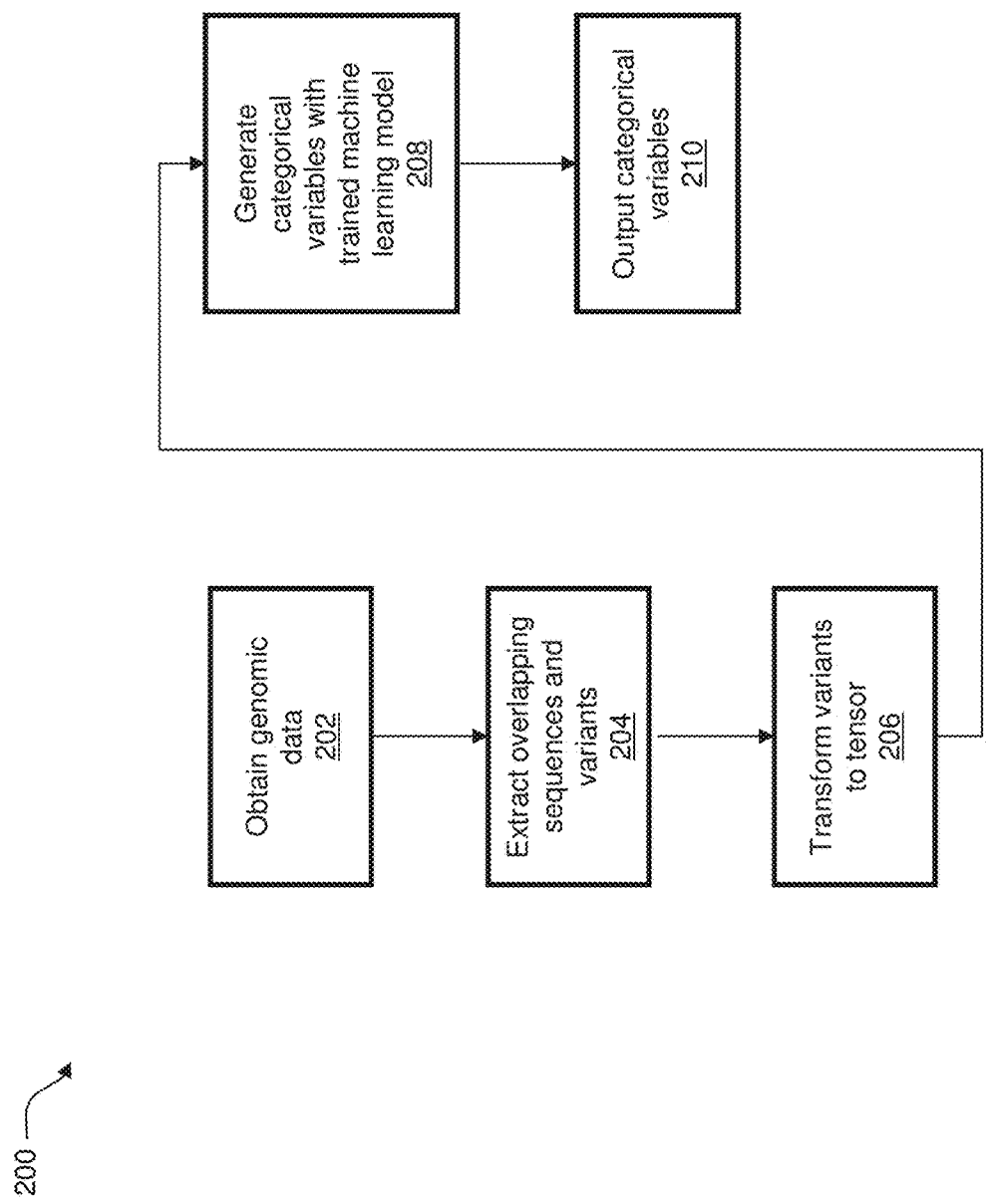
FIG. 2 is a flow chart of a method for variant calling in single molecule sequencing using a convolutional neural network, in accordance with an embodiment.

Turning to FIG. 2, a flowchart for a method for variant calling in single molecule sequencing using a convolutional deep neural network 200.

At block 202, the input module 150 obtains genomic data, for example, from the network interface 110, the input interface 106, or the database 116.

At block 204, the input module 150 extracts overlapping sequencing read alignments from the genomic data and determines variants where the read alignments differ. In further embodiments, the input module 150 obtains only the extracted variant data, for example, in Variant Call Format (VCF).

At block 206, the input module 150 transforms the overlapping sequencing read alignments and associated variants into a multi-dimensional tensor. In a particular case, a shape of the multi-dimensional tensor can have three dimensions; a first dimension corresponding to a position of a variant, a second dimension corresponding to a count of a base (A, C, G, or T) on a sequencing read, and a third dimension corresponding to different ways of counting bases. In some cases, the shape of the multi-dimensional tensor can be 33 by 4 by 4 for the first dimension, second dimension, and third dimension, respectively. In these cases, the first dimension representing a total comprising a candidate variant and flanking base-pairs added to both sides of the candidate.

At block 208, the machine learning module 152 passes the multi-dimensional tensor through a trained machine learning architecture to generate categorical output variables by minimizing a cost function iterated over each variant. The categorical output variables can include at least one of: alternate base at a single-nucleotide polymorphism, zygosity of a variant, variant type, and length of an indel. In some cases, these output variables can be represented by a vector (for example, with a one-dimensional tensor) using one-hot or probability encoding. The machine learning architecture trained using a genomic dataset with previously identified variants (i.e., truth variants). In an embodiment, for the training dataset, each truth variant was paired with two non-variants randomly sampled from the genome at all possible non-variant and non-ambiguous sites. In an embodiment, a minority (for example, 10%) of the training dataset was used instead for validation of the machine learning model.

In an embodiment, the machine learning architecture includes a convolutional neural network comprising an input layer feeding sequential convolutional and pooling layers, which feed at least one regression and classification layer. In a particular case, the machine learning architecture includes three convolutional layers, each followed by pooling layers, and at least two fully-connected layers. In a particular case, each convolutional layer using an SELU activation function. In this case, the prediction for alternate base at a single-nucleotide polymorphism is predicted from the first fully-connected layer and the predictions for zygosity of the variant, variant type, and length of the indel are predicted from the second fully-connected layer. In some cases, the fully-connected layers can use batch normalization, such as SELU activation functions or sigmoid activation functions, and dropout techniques.

At block 210, the output module 154 outputs the categorical output variables of the trained machine learning architecture.

In some cases, visualizations of the output of the system 100 can be generated. For example, an interactive python notebook accessible within a web browser or a command line script for visualizing inputs and their corresponding node activations in hidden layers and output layers. In an example, the visualization can show the input and node activations in all hidden layers and output layers of an A>G SNP variant in sample HG002 test against a model trained with samples from HG001 for a thousand epochs at $1e^{-3}$ learning rate. Each of the nodes can be considered as a feature deduced through a chain of nonlinear transformations of the read alignments input.

Advantageously, embodiments of the present disclosure can be substantially computationally efficient such that they can run on modern desktop and server computers with commodity configurations. In some cases, implementations of the system 100 can be roughly divided into two groups, one is sample preparation (preprocessing and model training), and the second is sample evaluation (model evaluation and visualization). Model training runs efficiently because it can invoke optimized techniques; for example, Tensorflow, which is maintained by a large developer community and has been intensively optimized. In some cases, sample preprocessing was determined to be more efficient if using specialized compilers; for example, by using Pypy36, a Just-In-Time (JIT) compiler that performs as an alternative to the native python interpreter. In example experiments, Pypy sped up sample preparation by 5 to 10 times.

Generally, memory consumption in model training can be a concern. For example, with a naïve encoding, HG001 requires 40 GB memory to store the variant and non-variant samples, which could prevent effective GPU utilization. The present inventors observed that, in some cases, these samples are immutable and follow the "write once, read many" access pattern. Thus, in some cases, the system 100 can apply in-memory compression; for example, using the blosc37 library with the lz4hc compression algorithm, which provides a high compression ratio, 100 MB/s compression rate, and an ultra-fast decompression rate at 7 GB/s. Example experiments conducted by the present inventors show that applying in-memory compression does not impact the speed but decreased the memory consumption by five times.

The present inventors conducted an example experiment to verify the use of the present embodiments. As part of the example experiment, the present embodiments were benchmarked on DNA sequencing datasets using three different example sequencing technologies: Illumina, PacBio, and ONT. Illumina is an example "next-generation sequencing" (NGS) technology and PacBio and ONT are example "single molecule sequencing" (SMS) technologies. SMS generally produces much longer sequencing reads and generally easier in terms of sample preparation. However, for SMS, the error rate is presently very high at 10-15% in comparison to NGS, which is less than 1%. Advantageously, the present embodiments can provide a suitable error rate to do variant calling using SMS.

The example experiments use the Genome-in-a-Bottle (GIAB) dataset. GIAB is a project that produces sequencing data of all available sequencing technologies of a few standard samples with known variants. The GIAB dataset provides high-confidence SNPs and indels for a standard reference sample HG001 (also referred to as NA12878) by integrating and arbitrating between 14 datasets from five sequencing and genotyping technologies, seven read mappers and three variant callers. For the example experiments, the training dataset (also referred to as the truth dataset) used dataset version 3.3.2 for HG001 that comprises 3,042,789 SNPs, 241,176 insertions and 247,178 deletions for the GRCh38 reference genome, along with 3,209,315 SNPs, 225,097 insertions and 245,552 deletions for GRCh37. The dataset also provides a list of regions that cover 83.8% and 90.8% of the GRCh38 and the GRCh37 reference genome, where variants were confidently genotyped. The GIAB extensive project was also used that further introduced four standard samples, including the Ashkenazim Jewish sample HG002, containing 3,077,510 SNPs, 249,492 insertions and 256,137 deletions for GRCh37, 3,098,941 SNPs, 239,707 insertions and 257,019 deletions for GRCh38. 83.2% of the whole genome was marked as confident for both the GRCh37 and GRCh38.

The example experiments use the Illumina technology produced by the National Institute of Standards and Technology (NIST) and Illumina. Both the HG001 and HG002 datasets were generated on an Illumina HiSeq 2500 in Rapid Mode (v1) with 2×148 bp paired-end reads. Both have approximately 300× total coverage and were aligned to GRCh38 decoy version 1 using Novoalign version 3.02.07. In the example experiments, the two datasets were further down-sampled to 50× to match the available data coverage of the other two SMS.

The example experiments use the Pacific Bioscience (PacBio) technology that was produced by NIST and Mt. Sinai School of Medicine. The HG001 dataset has 44× coverage, and the HG002 has 69×. Both datasets comprise 90% P6-C4 and 10% P5-C3 sequencing chemistry and have a sequence N50 length between 10 k-11 kbp. Reads were extracted from the downloaded alignments and aligned again to GRCh37 decoy version 5 using NGMLR version 0.2.3.

The example experiments use the Oxford Nanopore (ONT) technology that was generated by the Nanopore WGS consortium. Only data for sample HG001 are available to date, thus limiting the "cross sample variant calling evaluation" and "combined sampled training" on ONT data. The example experiments used the 'rel3' release sequenced on the Oxford Nanopore MinION using 1D ligation kits (450 bp/s) and R9.4 chemistry. The release comprises 39 flowcells and 91.2 G bases, about 30× coverage. The reads were downloaded in raw fastq formatted and aligned to GRCh37 decoy version 5 using NGMLR version 0.2.3.

In the example experiments, 'good performance' implies correct predictions could be made even when the evidence is marginal to distinguish a genuine variant from non-variant (reference) position. To achieve this goal, the present inventors paired each truth variant with two non-variants randomly sampled from the genome at all possible non-variant and non-ambiguous sites for model training. With about 3.5 M truth variants from the GIAB dataset, about 7 M non-variants are added as samples for training of the CNN model. In this case, pairing two non-variants with a variant was used to teach the CNN to prefer a non-variant decision when the odds of making either decisions are even.

For the example experiments, the present inventors randomly partitioned all samples into 90% for training and 10% for validation. In this case, different datasets were used for testing samples. For example, in the example experiments, the samples of HG002 were used to test against a model trained on HG001, and vice versa.

The benchmarking was conducted at common variant sites from 1000 Genomes Project phase 3 with minor allele frequency ≥5%. The system's 100 performance to call variants genome-wide was examined. In addition, other variants caller approaches were examined for comparison. Tests were conducted to determine: 1) what are the characteristics of false positives and false negatives; 2) can lower learning rate and longer training provide better performance; 3) can a model train on truth variants from multiple samples provide better performance; 4) can a higher input data quality improve the variant calling performance; and 5) is the current network design sufficient in terms of learning capacity.

For the example experiments, GPU acceleration was used for model training and CPU-only was used for variant calling. Using a high-performance desktop GPU model GTX 1080 Ti, 170 seconds are needed per epoch, which leads to about 5 hours to finish training a model with the fast training mode. However, for variant calling the speed up by GPU is insignificant because CPU workloads such as VCF file formatting and I/O operations dominate. Variant calling at 8.5 M common variant sites takes about 40 minutes using 28 CPU cores. Variant calling genome-wide varies between 30 minutes to a few hours subject to which sequencing technology and alternative allele frequency cutoff were used.

In the example experiments, the present embodiments were benchmarked on three sequencing technologies: Illumina, PacBio, and ONT using both the fast and the nonstop training mode. In nonstop training mode, training the model was started from 0 to 999-epoch at learning rate $1e^{-3}$, then to 1499-epoch at $1e^{-4}$, and finally to 1999-epoch at $1e^{-5}$. The model generated by the fast mode was then benchmarked, and all three models stopped at different learning rates in the nonstop mode. Variant calling was also benchmarked on one sample (e.g., HG001) using a model trained on another sample (e.g., HG002). Further, a GATK UnifiedGenotyper and GATK HaplotypeCaller were benchmarked for comparison. Noteworthy, GATK UnifiedGenotyper was superseded by GATK HaplotypeCaller, thus for Illumina data, one should refer to the results of HaplotypeCaller as the true performance of GATK. However, the experimental benchmarks show that UnifiedGenotyper performed better than HaplotypeCaller on the PacBio and ONT data, thus UnifiedGenotyper was also benchmarked for all three technologies to make parallel comparisons. A benchmark was also determined for SMS reads using the Nanopolish v0.9.0 tool.

In the example experiments, as described herein, benchmarks at common variant sites from 1000 Genomes Project phase 3 with global MAF (minor allele frequency) ≥5% (8,511,819 sites for GRCh37, 8,493,490 sites for GRCh38, hereafter referred to as "1KGp3") demonstrate the performance of the present embodiments on a typical precision medicine application, where tens to hundreds of known clinically relevant or actionable variants are being genotyped. This is becoming increasingly important as SMS is becoming more widely used for clinical diagnosis of structural variations, but at the same time, doctors and researchers also want to know if there exist any actionable or incidental small variants without additional short read sequencing. So firstly, the present embodiments were evaluated on common variant sites before extending the evaluation genome-wide.

In the example experiments, vcfeval in RTG Tools version 3.7 was used to benchmark the results and generate five metrics including FPR (False Positive Rate), FNR (False Negative Rate), Precision, Recall, and F1-score. From the RTG vcfeval also provides the best variant quality cutoff for each dataset, filtering the variants under which can maximize the F1-score.

TABLE 1 shows example results for the performance of the present embodiments in the example experiment on Illumina data. In this experiment, the best accuracy was shown to be achieved by calling variants in HG001 using the model trained on HG001 at 999-epoch, with 0.25% FPR, 0.41% FNR, 99.75% precision and 99.67% F1-score. Generally, a major concern of using deep learning or any statistical learning technique for variant calling is the potential for overfitting to the training samples. The present results show that the present embodiments were not affected by overfitting, and the versatility of the trained models were validated by calling variants in a genome using a model trained on a second sample. The gap of FNR between the present embodiments and GATK UnifiedGenotyper on HG001 is 0.68% (3.11% against 2.43%) but enlarged to 3.27% (5.80% against 2.52%) on HG002.

TABLE 1

| Seq. Tech. | Model Trained on | Trained Epochs | Ending Learning Rate and Lambda | Call Variants in | Best Variant Quality Cutoff | Overall FPR % | Overall FNR % | Overall Precision % | Overall F1 Score % | SNP FPR % | SNP FNR % | SNP Precision % | SNP F1 Score % | Indel FPR % | Indel FNR % | Indel Precision % | Indel F1 Score % |
|---|---|---|---|---|---|---|---|---|---|---|---|---|---|---|---|---|---|
| Illumina | HG001 | 67* | 1.E−05 | HG001 | 67 | 0.28 | 0.45 | 99.72 | 99.64 | .07 | .10 | 99.9 | 99.9 | 1.9 | 3.3 | 98.0 | 97.3 |
|  |  | 999 | 1.E−03 |  | 119 | 0.25 | 0.41 | 99.75 | 99.67 | .08 | .08 | 99.9 | 99.9 | 1.6 | 3.1 | 98.3 | 97.5 |
|  |  | 1499 | 1.E−04 |  | 128 | 0.28 | 0.41 | 99.72 | 99.66 | .08 | .08 | 99.9 | 99.9 | 1.8 | 3.1 | 98.0 | 97.4 |
|  |  | 1999 | 1.E−05 |  | 147 | 0.29 | 0.42 | 99.71 | 99.64 | .08 | .09 | 99.9 | 99.9 | 1.9 | 3.2 | 97.9 | 97.3 |
|  | HG001 | 67* | 1.E−05 | HG002 | 58 | 0.32 | 0.51 | 99.68 | 99.59 | .11 | .15 | 99.8 | 99.8 | 2.1 | 3.5 | 97.8 | 97.1 |
|  |  | 999 | 1.E−03 |  | 107 | 0.30 | 0.49 | 99.70 | 99.61 | .11 | .14 | 99.8 | 99.8 | 1. | 3.4 | 97.9 | 97.2 |
|  |  | 1499 | 1.E−04 |  | 151 | 0.34 | 0.54 | 99.66 | 99.56 | .11 | .16 | 99.8 | 99.8 | 2.2 | 3.8 | 97.6 | 96.9 |
|  |  | 1999 | 1.E−05 |  | 147 | 0.37 | 0.54 | 99.63 | 99.55 | .12 | .15 | 99.8 | 99.8 | 2.4 | 3.8 | 97.4 | 96.7 |
|  | HG002 | 66* | 1.E−05 | HG001 | 53 | 0.31 | 0.80 | 99.69 | 99.44 | .08 | .14 | 99.9 | 99.8 | 2.1 | 6.2 | 97.6 | 95.6 |
|  |  | 999 | 1.E−03 |  | 96 | 0.28 | 0.76 | 99.72 | 99.48 | .07 | .13 | 99.9 | 99.9 | 2.0 | 6.0 | 97.8 | 95.9 |
|  |  | 1499 | 1.E−04 |  | 134 | 0.33 | 0.81 | 99.67 | 99.43 | .08 | .15 | 99. | 99.8 | 2.3 | 6.3 | 97.4 | 95.5 |
|  |  | 1999 | 1.E−05 |  | 148 | 0.35 | 0.83 | 99.65 | 99.41 | .08 | .15 | 99.9 | 99.8 | 2.5 | 6.5 | 97.3 | 95.3 |
|  | HG002 | 66* | 1.E−05 | HG002 | 54 | 0.28 | 0.76 | 99.72 | 99.48 | .07 | .13 | 99.9 | 99.9 | 2.0 | 6.1 | 97.8 | 95.8 |
|  |  | 999 | 1.E−03 |  | 99 | 0.24 | 0.72 | 99.76 | 99.52 | .06 | .13 | 99.9 | 99.9 | 1.7 | 5.8 | 98.1 | 96.1 |
|  |  | 1499 | 1.E−04 |  | 124 | 0.27 | 0.72 | 99.73 | 99.50 | .07 | .12 | 99.9 | 99.9 | 1.9 | 5.8 | 97.9 | 95.9 |
|  |  | 1999 | 1.E−05 |  | 132 | 0.28 | 0.73 | 99.72 | 99.50 | .07 | .12 | 99.9 | 99.9 | 2.0 | 5.9 | 97.8 | 95.9 |
| DeepVariant |  |  |  |  | 3 | 0.04 | 0.06 | 99.96 | 99.95 | 0.0 | 0.0 | 99.9 | 99.9 | 0.2 | 0.2 | 99.7 | 99.7 |
| LoFreq |  |  |  |  | Benchmarked SNP only |  |  |  |  | 10 | 0.5 | 85.0 | 91.6 | — | — | — | — |
| GATK UnifiedGenotyper, HG001 |  |  |  |  | 3 | 0.19 | 0.35 | 99.81 | 99.73 | 0.1 | 0.1 | 99.9 | 99.9 | 0.8 | 2.4 | 99.1 | 98.3 |
| GATK HaplotypeCaller, HG001 |  |  |  |  | 4 | 0.07 | 0.11 | 99.93 | 99.91 | 0.0 | 0.0 | 99.9 | 99.9 | 0.5 | 0.6 | 99.4 | 99.4 |
| GATK UnifiedGenotyper, HG002 |  |  |  |  | 3 | 0.20 | 0.37 | 99.80 | 99.71 | 0.1 | 0.1 | 99.8 | 99.8 | 0.7 | 2.5 | 99.2 | 98.3 |
| GATK HaplotypeCaller, HG002 |  |  |  |  | 5 | 0.07 | 0.10 | 99.93 | 99.92 | 0.0 | 0.1 | 99.9 | 99.9 | 0.3 | 0.5 | 99.6 | 99.5 | where * represents fast training mode.

number of true positives (TP), false positives (FP), true negatives (TN), and false negatives (FN), the five metrics were determined as FPR=FP÷(FP+TN), FNR=FN≥(FN+TP), Precision=TP≥(TP+FP), Recall=TP≥(TP+FN), and $$F1\text{-score} = \frac{2TP}{2TP + FN + FP}.$$

TP was defined as variants existing in both 1KGp3 and GIAB dataset that identified as a variant with no discrepancy in terms of allele, type, zygosity and indel length if applicable. TN was defined as variants existing in 1KGp3 but not in the GIAB dataset that identified as a non-variant. FP was defined as 1) sites supposed to be TN but identified as variant, or 2) variants existing in the GIAB dataset that also identified as a variant, but with discrepant variant type, alternative allele or zygosity. FN was defined as the variants existing in the GIAB dataset but identified as a non-variant. F1-score is the harmonic mean of the precision and recall.

TABLE 2 shows example results for the performance of the present embodiments in the example experiment on PacBio data. In this experiment, the best accuracy was shown to be achieved by calling variants in HG001 using the model trained on HG001 at 1499-epoch, with 2.17% FPR, 6.06% FNR, 97.70% precision and 95.78% F1-score. For comparison, DeepVariant has been reported to have benchmarked the same dataset and reported 97.25% precision, 88.51% recall (11.49% FNR) and 92.67% F1-score. The present benchmark differs from DeepVariant because Indels >4 bp have been removed (e.g. 52,665 sites for GRCh38 and 52,709 for GRCh37 in HG001) from both the baseline and variant calls. If one were to assume DeepVariant can identify all the 91 k Indels >4 bp correctly, the recall of DeepVariant would increase to 90.73% (9.27% FNR), which is still 3.21% lower than the present embodiments. The SNP calling F1-score on PacBio data for the present embodiments topped at 99.28% for HG001 and 99.30% for HG002, illustrating that the present embodiments can be suitable for genotyping SNPs sensitively and accurately at known clinically relevant or actionable variants using PacBio reads in precision medicine applications.

TABLE 2

| Seq. Tech. | Model Trained on | Trained Epochs | Ending Learning Rate and Lambda | Call Variants in | Best Variant Quality Cutoff | Overall FPR % | Overall FNR % | Overall Precision % | Overall F1 Score % | SNP FPR % | SNP FNR % | SNP Precision % | SNP F1 Score % | Indel FPR % | Indel FNR % | Indel Precision % | Indel F1 Score % |
|---|---|---|---|---|---|---|---|---|---|---|---|---|---|---|---|---|---|
| PacBio | HG001 | 50* | 1.E−05 | HG001 | 69 | 1.51 | 7.41 | 98.38 | 95.39 | .32 | 1.4 | 99.6 | 99.1 | 10 | 60 | 76 | 97.3 |
| | | 999 | 1.E−03 | | 94 | 1.39 | 7.07 | 98.51 | 95.64 | .26 | 1.2 | 99.7 | 99.2 | 10 | 58 | 78.2 | 97.5 |
| | | 1499 | 1.E−04 | | 89 | 2.17 | 6.06 | 97.70 | 95.78 | .25 | 1.1 | 99.7 | 99.2 | 16 | 49 | 72.0 | 97.4 |
| | | 1999 | 1.E−05 | | 85 | 2.43 | 5.81 | 97.43 | 95.78 | .26 | 1.1 | 99.7 | 99.2 | 18 | 46 | 70.4 | 97.3 |
| | HG001 | 50* | 1.E−05 | HG002 | 75 | 1.78 | 7.48 | 98.07 | 95.22 | .71 | 1.4 | 99.2 | 98.9 | 10 | 60 | 77.7 | 97.1 |
| | | 999 | 1.E−03 | | 96 | 1.98 | 7.31 | 97.87 | 95.21 | .75 | 1.4 | 99.2 | 98.8 | 11 | 58 | 76.0 | 97.2 |
| | | 1499 | 1.E−04 | | 114 | 2.07 | 7.77 | 97.76 | 94.91 | .76 | 1.4 | 99.2 | 98.8 | 12 | 63 | 72.6 | 96.9 |
| | | 1999 | 1.E−05 | | 123 | 1.97 | 7.94 | 97.86 | 94.87 | .75 | 1.4 | 99.2 | 98.9 | 11 | 64 | 73.0 | 96.7 |
| | HG002 | 72* | 1.E−05 | HG001 | 56 | 1.63 | 9.22 | 98.20 | 94.35 | .49 | 2.5 | 99.4 | 98.4 | 10 | 68 | 72.4 | 95.6 |
| | | 999 | 1.E−03 | | 99 | 1.69 | 8.47 | 98.16 | 94.73 | .57 | 1.8 | 99.4 | 98.7 | 10 | 67 | 73.3 | 95.9 |
| | | 1499 | 1.E−04 | | 116 | 2.43 | 8.25 | 97.36 | 94.47 | .80 | 1.9 | 99.1 | 98.6 | 14 | 64 | 66.9 | 95.5 |
| | | 1999 | 1.E−05 | | 127 | 2.34 | 8.57 | 97.45 | 94.34 | .89 | 2.0 | 99.0 | 98.5 | 13 | 66 | 68.0 | 95.3 |
| | HG002 | 72* | 1.E−05 | HG002 | 55 | 1.88 | 7.08 | 97.98 | 95.38 | .55 | 1.2 | 99.4 | 99.1 | 12 | 58 | 75.2 | 95.8 |
| | | 999 | 1.E−03 | | 88 | 1.86 | 6.59 | 98.01 | 95.66 | .49 | 1.1 | 99.5 | 99.1 | 12 | 54 | 76.3 | 96.1 |
| | | 1499 | 1.E−04 | | 101 | 2.02 | 5.81 | 97.85 | 95.99 | .42 | 1.0 | 99.5 | 99.3 | 14 | 47 | 76.1 | 95.9 |
| | | 1999 | 1.E−05 | | 101 | 2.05 | 5.70 | 97.83 | 96.03 | .41 | 0.9 | 99.5 | 99.3 | 14 | 46 | 75.9 | 95.9 |
| GATK UnifiedGenotyper, HG001 | | | | | 3 | 0.83 | 99.92 | 8.19 | 0.15 | .94 | 99 | 8.19 | 0.17 | — | — | — | — |
| GATK HaplotypeCaller, HG001 | | | | | 4 | 0.08 | 97.91 | 52.26 | 4.02 | .06 | 97 | 61.1 | 4.53 | 0.6 | 99 | 0.39 | 0.04 |
| GATK UnifiedGenotyper, HG002 | | | | | 3 | 0.75 | 99.91 | 9.91 | 0.17 | .85 | 99 | 9.91 | 0.19 | — | — | — | — |
| GATK HaplotypeCaller, HG002 | | | | | 5 | 0.69 | 98.74 | 63.81 | 2.47 | .79 | 98 | 63.8 | 2.78 | .02 | 100 | 15.6 | 0.00 | where * represents fast training mode.

TABLE 3 shows example results for the performance of the present embodiments in the example experiment on ONT data. As there are no publicly available deep coverage ONT datasets for HG002, the example experiment benchmarked variant calls in the chromosome 1 of HG001 using models trained on all chromosomes of HG001 except for the chromosome 1. The best F1-score, 90.53%, was witnessed to be achieved at 1999-epoch, with FPR 2.96%, FNR 14.78% and precision 96.55%. For comparison, the present inventors applied Nanopolish to the whole genome of HG001, using 24 CPU cores and a peak of 160 GB memory, and determined that Nanopolish finished in 4.5 days and achieved 0.04%, 21.57%, 97.51%, and 86.93% on FPR, FNR, precision and F1-score, respectively.

non-variant even in the presence of sequencing errors or other artificial signals. Instead of naively evaluating all three billion sites of the whole genome, the example experiment tested the performance at different alternative allele cutoffs for all three sequencing technologies. As expected, a higher allele cutoff speeds up variant calling by producing fewer candidates to be tested but worsens recall especially for noisy data like PacBio and ONT. The example experiments provide a reference point on how to choose a cutoff for each sequencing technology to achieve a good balance between recall and running speed. Precision, Recall and F1-score metrics were used but FPR (calculated as FP÷(FP+TN)) was not used because FP becomes negligibly small compare to TN, which is around three billion in human genome-wide

TABLE 3

| Seq. Tech. | Model Trained on | Trained Epochs | Ending Learning Rate and Lambda | Call Variants in | Best Variant Quality Cutoff | Overall FPR % | Overall FNR % | Overall Precision % | Overall F1 Score % | SNP FPR % | SNP FNR % | SNP Precision % | SNP F1 Score % | Indel FPR % | Indel FNR % | Indel Precision % | Indel F1 Score % |
|---|---|---|---|---|---|---|---|---|---|---|---|---|---|---|---|---|---|
| ONT | HG001 (except chr1) | 110* | 1.E−05 | HG001 (chr1) | 47 | 3.40 | 17.09 | 95.93 | 88.94 | 3.3 | 9.2 | 96.3 | 93.4 | 3.9 | 86.4 | 76.59 | 23.07 |
| | | 999 | 1.E−03 | | 53 | 4.05 | 16.31 | 95.20 | 89.07 | 3.7 | 8.9 | 95.8 | 93.3 | 6.2 | 81.7 | 73.19 | 29.28 |
| | | 1499 | 1.E−04 | | 70 | 2.95 | 14.99 | 96.55 | 90.41 | 2.5 | 7.7 | 97.2 | 94.6 | 6.3 | 79.2 | 75.46 | 32.51 |
| | | 1999 | 1.E−05 | | 74 | 2.96 | 14.78 | 96.55 | 90.53 | 2.5 | 7.5 | 97.2 | 94.7 | 6.6 | 78.6 | 74.90 | 33.24 |
| Nanopolish, HG001 | | | | | 20 | 0.04 | 21.57 | 97.51 | 86.93 | .03 | 15 | 98.1 | 90.7 | 0.1 | 63.4 | 88.57 | 51.73 |
| DeepVariant (chr1) | | | | | 3 | 0.22 | 23.82 | 96.26 | 85.05 | .21 | 15 | 96.7 | 90.3 | 0.3 | 89.1 | 72.98 | 18.95 |
| LoFreq | | | | | — | Benchmarking SNP only | | | | 2.7 | 46.9 | 90.6 | 66 | — | — | — | |
| GATK UnifiedGenotyper, HG001 | | | | | 1 | 3.66 | 84.44 | 80.07 | 26.05 | 4.1 | 82 | 80.0 | 28.7 | — | — | — | — |
| GATK HaplotypeCaller, HG001 | | | | | 1 | 0.41 | 98.65 | 76.04 | 2.65 | .45 | 98 | 76.7 | 2.9 | 0.1 | 99.9 | 9.59 | 0.03 |
| Nanopolish, afcut0.2, depthcut4, chr19 | | | | | 20 | 0.15 | 34.13 | 90.00 | 76.07 | .08 | 27 | 94.5 | 82.2 | 0.7 | 83.0 | 36.45 | 23.13 |
| Nanopolish, 1 kgp3, chr19 | | | | | 20 | 0.08 | 22.71 | 95.28 | 85.35 | .05 | 16 | 96.8 | 89.7 | 0.3 | 66.7 | 73.64 | 45.79 | where * represents fast training mode.

Beyond benchmarking variants at sites known to be variable in a sample, the example experiments also benchmarked performance of the present embodiments on calling variants genome-wide. Calling variants genome-wide is challenging because it tests not only how good the system 100 can derive the correct variant type, zygosity and alternative allele of a variant when evidence is marginal, but also in reverse, how good the system 100 can filter/suppress a variant identification. All models were trained for 1000 epochs with learning rate at 1 e-3. The example experiments were performed on two Intel Xeon E5-2680 v4 using all 28 cores.

Example results for the performance of the present embodiments in the example experiments on calling variants genome-wide are shown in TABLE 4. As expected, with higher alternative allele frequency threshold (0.2), the precision was higher while the recall and time consumption was reduced in all experiments. In this example experiment, for Illumina data, the best F1-score (with 0.2 allele frequency) achieved for the present embodiments was 98.65% for HG001 and 98.61% for HG002. The runtime varied between half and an hour (40 minutes for the best F1-score). While GATK HaplotypeCaller achieved highest performance on Illumina data, achieving an F1-score 99.76% for HG001 and 99.70% for HG002, it required a runtime of about 8 hours. Inspecting the false positive and false negative variant calls for the present embodiments, it was determined that it was about 0.19% for FP and 0.15% for FN.

(rel3), the best F1-score 77.89% was achieved at 0.1 frequency cutoff. However, the F1-score at 0.25 frequency cutoff is just slightly lower (76.95%), but ran about five times faster, from 13 hours to less than three hours. In these cases, the present inventors have determined that using 0.25 may be ideal as the frequency cutoff. The runtime is on average about 1.5 times longer than PacBio, due to the higher level of noise in data. Using the new rel5 ONT with better base calling quality, the best F1-score has increased from 87.26% (9.37% higher than rel3). The recall of SNP and the precision of Indel were the most substantially increased.

TABLE 4

| Seq. Tech | Train using Variants in | Call Variants in | Alt. Allele Freq. Cutoff | Best Variant Quality Cutoff | Time Consumption | Overall Precision % | Overall Recall % | Overall F1 Score % | SNP Precision % | SNP Recall % | SNP F1 Score % | Indel Precision % | Indel Recall % | Indel F1 Score % |
|---|---|---|---|---|---|---|---|---|---|---|---|---|---|---|
| Illumina | HG001 | HG001 | 0.1 | 189 | 1:08 | 98.2 | 98.9 | 98.6 | 98.1 | 99.9 | 99.0 | 98.6 | 96.9 | 97.7 |
| | | | 0.2 | 182 | 0:43 | 98.4 | 98.9 | 98.7 | 98.4 | 99.9 | 99.1 | 98.7 | 95.1 | 96.8 |
| | | | 0.25 | 180 | 0:26 | 98.7 | 98.0 | 98.3 | 98.7 | 99.8 | 99.2 | 98.6 | 87.3 | 92.6 |
| | | HG002 | 0.1 | 192 | 1:11 | 98.1 | 98.8 | 98.5 | 98.1 | 99.8 | 98.9 | 98.5 | 96.5 | 97.5 |
| | | | 0.2 | 183 | 0:41 | 98.4 | 98.8 | 98.6 | 98.3 | 99.8 | 99.0 | 98.5 | 94.9 | 96.6 |
| | | | 0.25 | 182 | 0:30 | 98.7 | 97.9 | 98.3 | 98.7 | 99.7 | 99.1 | 98.4 | 87.3 | 92.5 |
| | HG002 | HG001 | 0.1 | 198 | 1:16 | 98.6 | 98.5 | 98.5 | 98.7 | 99.9 | 99.2 | 97.9 | 93.3 | 95.6 |
| | | | 0.2 | 192 | 0:47 | 98.8 | 98.4 | 98.6 | 98.8 | 99.9 | 99.3 | 98.0 | 91.6 | 94.7 |
| | | | 0.25 | 184 | 0:25 | 98.9 | 97.6 | 98.3 | 99.1 | 99.8 | 99.4 | 97.9 | 85.0 | 91.0 |
| | | HG002 | 0.1 | 195 | 1:07 | 98.5 | 98.6 | 98.6 | 98.6 | 99.9 | 99.2 | 98.1 | 93.7 | 95.9 |
| | | | 0.2 | 188 | 0:44 | 98.7 | 98.5 | 98.6 | 98.8 | 99.8 | 99.2 | 98.2 | 92.2 | 95.1 |
| | | | 0.25 | 182 | 0:25 | 99.0 | 97.7 | 98.3 | 99.0 | 99.7 | 99.3 | 98.1 | 85.7 | 91.5 |
| | GATK UnifiedGenotyper, HG001 | | | 51 | 0:46 | 99.4 | 99.4 | 99.4 | 99.4 | 99.4 | 99.5 | 99.9 | 96.4 | 97.6 |
| | GATK HaplotypeCaller, HG001 | | | 5 | 8:45 | 99.6 | 99.8 | 99.7 | 99.8 | 99.8 | 99.8 | 100 | 98.9 | 99.0 |
| | GATK UnifiedGenotyper, HG002 | | | 4 | 0:46 | 98.7 | 99.4 | 98.8 | 99.4 | 99.1 | 98.7 | 99.8 | 96.5 | 97.7 |
| | GATK HaplotypeCaller, HG002 | | | 5 | 8:23 | 99.5 | 99.8 | 99.6 | 99.8 | 99.7 | 99.6 | 99.9 | 99.2 | 99.3 |
| PacBio | HG001 | HG001 | 0.1 | 157 | 9:46 | 96.3 | 88.6 | 92.3 | 96.7 | 99.5 | 98.0 | 79.1 | 31.1 | 44.6 |
| | | | 0.2 | 130 | 3:53 | 98.1 | 87.6 | 92.6 | 99.0 | 96.6 | 97.7 | 75.8 | 31.5 | 44.5 |
| | | | 0.25 | 125 | 2:01 | 98.6 | 83.1 | 90.2 | 99.4 | 91.4 | 95.2 | 78.5 | 27.1 | 40.3 |
| | | HG002 | 0.1 | 153 | 9:24 | 97.0 | 89.1 | 92.9 | 97.9 | 99.2 | 98.5 | 71.5 | 34.2 | 46.3 |
| | | | 0.2 | 132 | 3:34 | 97.9 | 88.3 | 92.9 | 99.0 | 97.1 | 98.0 | 73.3 | 34.0 | 46.5 |
| | | | 0.25 | 116 | 1:46 | 98.1 | 84.7 | 90.9 | 99.2 | 92.5 | 95.7 | 75.5 | 31.2 | 44.2 |
| | HG002 | HG001 | 0.1 | 163 | 14:55 | 95.6 | 86.7 | 90.9 | 96.6 | 99.0 | 97.7 | 59.1 | 24.5 | 34.6 |
| | | | 0.2 | 147 | 3:29 | 97.5 | 85.6 | 91.2 | 98.9 | 96.1 | 97.5 | 58.2 | 23.6 | 33.6 |
| | | | 0.25 | 139 | 1:39 | 98.2 | 81.5 | 89.0 | 99.3 | 90.9 | 94.9 | 66.3 | 21.1 | 32.0 |
| | | HG002 | 0.1 | 150 | 15:31 | 97.1 | 89.3 | 93.0 | 98.3 | 99.1 | 98.7 | 69.1 | 39.7 | 50.5 |
| | | | 0.2 | 134 | 3:34 | 98.1 | 88.5 | 93.1 | 99.4 | 97.3 | 98.3 | 72.2 | 36.5 | 48.5 |
| | | | 0.25 | 118 | 1:46 | 98.2 | 84.8 | 91.0 | 99.5 | 92.8 | 96.0 | 72.9 | 31.4 | 43.9 |
| Oxford Nanopore (rel3) | HG001 | HG001 | 0.1 | 140 | 13:01 | 86.2 | 71.0 | 77.9 | 86.8 | 91.9 | 89.2 | 55.3 | 10.6 | 17.9 |
| | | | 0.2 | 139 | 4:47 | 87.2 | 70.2 | 77.8 | 87.7 | 88.0 | 87.8 | 59.0 | 9.90 | 16.9 |
| | | | 0.25 | 136 | 2:40 | 87.8 | 68.5 | 77.0 | 88.3 | 82.9 | 85.4 | 59.4 | 9.26 | 16.0 |
| | | | 0.35 | 130 | 1:30 | 91.0 | 57.4 | 70.4 | 91.3 | 65.8 | 76.5 | 67.3 | 6.62 | 12.0 |
| Oxford Nanopore (rel5) | HG001 | HG001 | 0.2 | 162 | 5:53 | 88.8 | 85.8 | 87.3 | 88.9 | 93.8 | 91.2 | 72.1 | 8.32 | 14.9 |
| | | | 0.25 | 159 | 3:12 | 89.1 | 82.2 | 85.5 | 89.3 | 90.1 | 89.7 | 72.4 | 8.02 | 14.4 |
| | | | 0.35 | 148 | 1:51 | 91.2 | 67.9 | 77.8 | 91.5 | 75.2 | 82.5 | 71.2 | 6.54 | 11.9 |

Advantageously, as described herein, the neural network architecture of the present embodiments can be used as an orthogonal method to validate a variant for filtering or validating results to further increase accuracy.

In this example experiment, for the PacBio, the best F1-scores were also achieved at 0.2 allele frequency cutoff. The best F1-score is 92.57% for HG001 and 93.05% for HG002 running for ~3.5 hours. In contrast, DeepVariant has been reported to achieve 35.79% F1-score (22.14% precision, 93.36% recall) on HG001 with PacBio. The runtime for the present embodiments at 0.25 frequency cutoff is about 2 hours, which is about half the time consumption at 0.2 frequency cutoff, and about ⅕ the time consumption at 0.1 frequency cutoff. In this example experiment, for ONT The example experiments also benchmarked against a newer version of DeepVariant (v0.6.1). Generally, DeepVariant requires base-quality, thus it generally fails on the PacBio dataset, in which base-quality is not provided. On ONT data (rel5), DeepVariant performed much better than the traditional variant callers that were not designed for long reads, but it performed worse than the present embodiments. It was also found that DeepVariant's computational resource consumption on long reads is prohibitively high and, in the example experiments, it was only able to call variants in few chromosomes. For the example experiments using the newer version of Deep Variant, using transfer-learning, the present inventors trained two models for ONT data on chromosome 1 and 21 respectively, and called variants in chromosome 1 and 22 against the different models. In total three settings were benchmarked: 1) call variants in chromosome 1 against the chromosome 21 model, 2) call variants in chromosome 22 against the chromosome 21 model, and 3) call variants in chromosome 22 against the chromosome 1 model. Training the models required about 1.5 days until the validation showed a decreasing F1-score with further training. Using 24 CPU cores, the first step of variant calling generated 337 GB candidate variants data in 1,683 minutes for chromosome 1 and generated 53G data in 319 minutes for chromosome 21. The second step of variant calling took 1,171 and 213 minutes to finish for chromosome 1 and 22, respectively. The last step took 160 minutes and was very memory intensive, requiring 74 GB of RAM for chromosome 1. In terms of F1-score, DeepVariant has achieved 83.05% in chromosome 1, and 77.89% in chromosome 22, against the model trained on chromosome 21. The present inventors verified that more samples for model training do not lead to better variant calling performance, using the model trained on chromosome 1, the F1-score dropped slightly to 77.09% for variants in chromosome 22. Using the computational resource consumption on chromosome 1, it is estimated that the newer version of DeepVariant would require 4 TB storage and about one month for whole genome variant calling of a genome sequenced with long reads.

The example experiments further benchmarked three additional variant callers, including Vardict (v20180724), LoFreq (v2.1.3.1), and FreeBayes (v1.1.0-60-gc15b070). Vardict requires base quality, thus failed on the PacBio dataset, in which base quality is not provided. Vardict identified only 62,590 variants in the ONT dataset, among them only 231 variants are true positives. The results suggest Vardict is not yet ready for Single Molecule Sequencing long reads. To enable Indel calling in LoFreq, BAQ (Base Alignment Quality) needs to be calculated in advance. However, the BAQ calculation works only for Illumina reads, thus for LoFreq, it was only benchmarked in SNP calling. Meanwhile, LoFreq does not provide zygosity in the result, and thus the example experiments were prohibited from using "RTG vcfeval" for performance evaluation. Thus, a true positive in LoFreq was considered to be a matched truth record in 1) chromosome, 2) position and 3) alternative allele. LoFreq requires base quality, thus failed on the PacBio dataset, in which base quality is not provided. The results suggest that LoFreq is capable of SNP detection in Single Molecule Sequencing long reads. The example experiments were unable to finish running Freebayes on both the PacBio dataset and the ONT dataset after they failed to complete on either dataset after running for one month. According to the percentage of genome covered with variant calls, it is estimated that several months, 65 and 104 machine days on a latest 24-core machine, are required for a single PacBio and ONT dataset, respectively.

GIAB datasets were constructed from a consensus of multiple short-variant callers, thus tend to bias toward easy regions that are accessible. So, the example experiments also benchmarked the Syndip dataset, which is a benchmark dataset from the de novo PacBio assemblies of two homozygous human cell lines. The dataset provides a relatively more accurate and less biased estimate of small-variant-calling error rates in a realistic context. The results show that, when using Syndip variants for training, the performance of calling variants in both HG001 and HG002 at known variants are good. However, using the same model (Syndip), the performance dropped both at the Syndip known sites (excluding variants >4 bp, from 99.51% (HG001) to 98.52%) and for the whole genome (excluding variants >4 bp, from 94.88% (HG001) to 94.02%). The results support that Syndip contains variants that are harder to identify. In this way, in some cases, Syndip may be included when training models for the present embodiments to improve performance in the hard regions.

The truth SNPs and Indels provided by GIAB were intensively called and meticulously curated, and the accuracy and sensitivity of the GIAB datasets are unmatched. However, since the GIAB variants were generated without incorporating any SMS technology, it is possible that we can consummate GIAB by identifying variants not yet in GIAB, but specifically detected both by using the PacBio and the ONT data. For the HG001 sample (variants called in HG001 using a model trained on HG001), we extracted the so-called "false positive" variants (identified genome-wide with a 0.2 alternative allele frequency cutoff) called in both the PacBio and ONT dataset. Then we calculated the geometric mean of the variant qualities of the two datasets, and we filtered the variants with a mean quality lower than 135 (calculated as the geometric mean of the two best variant quality cutoffs, 130 and 139). The resulting catalog of 3,135 variants retained are listed in Supplementary Data 1. 2,732 are SNPs, 298 are deletions, and 105 are insertions. Among the SNPs, 1,602 are transitions, and 1,130 are transversions. The Ti/Tv ratio is ~1.42, which is substantially higher than random (0.5), suggesting a true biological origin. The top ten variants in quality was manually inspected using IGV to determine their authenticity (as illustrated in FIG. 5A). Among the ten variants, there is one convincing example at 2:163, 811,179 (GRCh37) that GIAB has previously missed. Another seven examples have weaker supports that need to be further validated using other orthogonal methods. Possible artifacts including 1) 7:89,312,043 has multiple SNPs in its vicinity, which is a typical sign of false alignment, 2) 1:566,371 20:3,200,689 (as illustrated in FIG. 5A) are located in the middle of homopolymer repeats, which could be caused by misalignment, 3) X:143,214,235 shows significant strand bias in Illumina data, and 4) X:140,640,513, X:143,218,136, and 9:113,964,088 are potential heterozygous variants but with allele frequency notably deviated from 0.5. Two examples are used because of the difference in representation: 13:104,270,904 and 10:65,260,789 have other GIAB truth variants in their 5 bp flanking regions. The example experiments show that the GIAB datasets are of superior quality and are the enabler of machine learning based downstream applications such as the present embodiments.

FIGS. 5A to 5D illustrate an Integrative Genomics Viewer (IGV) screen capture of selected variants. FIG. 5A illustrates a heterozygote SNP from T to G at chromosome 11, position 98,146,409 called only in the PacBio and ONT data, FIG. 5B illustrates a heterozygote deletion AA at chromosome 20, position 3,200,689 not called in all three technologies, FIG. 5C illustrates a heterozygote insertion ATCCTTCCT at chromosome 1, position 184,999,851 called only in the Illumina data, and FIG. 5D illustrates a heterozygote deletion G at chromosome 1, position 5,072,694 called in all three technologies. The tracks from top to down show the alignments of the Illumina, PacBio, and ONT reads from HG001 aligned to the human reference GRCh37.

Figure 6:
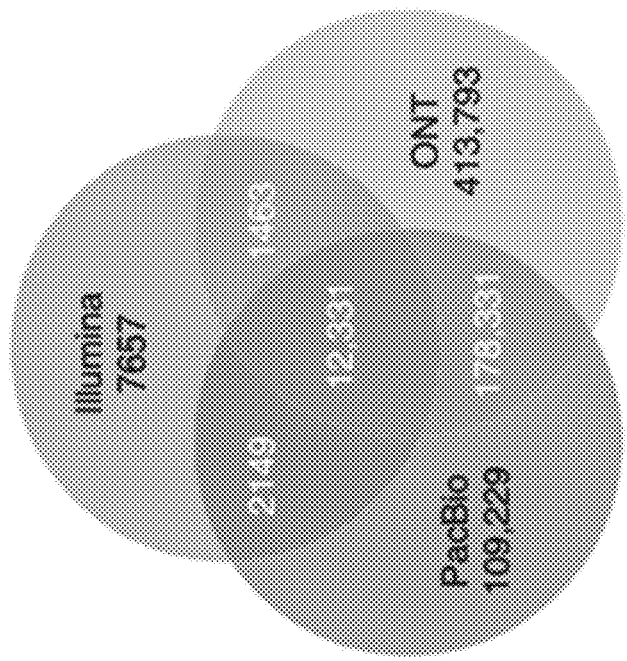
FIG. 6 illustrates an example Venn diagram showing the number of known variants undetected by different combinations of sequencing technologies, in accordance with the system of FIG. 1.

The present inventors, as part of the example experiments, also analyzed why the PacBio and ONT technologies cannot detect some variants. FIG. 6 shows the number of known variants undetected by different combinations of sequencing technologies. The genome sequence immediately after the variants was inspected and it was found that among the 12,331 variants undetected by all three sequencing technologies, 3,289 (26.67%) are located in homopolymer runs, and 3,632 (29.45%) are located in short tandem repeats. Among the 178,331 variants that cannot be detected by PacBio and ONT, 102,840 (57.67%) are located in homopolymer runs, and 33,058 (18.54%) are located in short tandem repeats. For Illustration, FIG. 5B depicts a known variant in homopolymer runs undetected by all three sequencing technologies, FIG. 5C depicts a known variant in short tandem repeats that cannot be detected PacBio and ONT, and FIG. 5D depicts a known variant flanked by random sequenced detected by all three sequencing technologies.

As evidenced by the example experiments, the present embodiments of a multi-task convolutional deep neural network for variant calling using single molecule sequencing has a performance at least on-par with GATK UnifiedGenotyper on Illumina data and outperforms Nanopolish and DeepVariant on PacBio and ONT data. Advantageously, the present embodiments have been experimentally verified to be the first method for SMS to finish a whole genome variant calling within two hours on a single CPU-only server, while providing better precision and recall than other variant callers such as Nanopolish. For the well-characterized NA12878 human sample, the present embodiments achieve 99.67%, 95.78%, 90.53% F1-score on 1KP common variants, and 98.65%, 92.57%, 87.26% F1-score for whole-genome analysis, using Illumina, PacBio, and Oxford Nanopore data, respectively. Training on a second human sample shows the present embodiments are sample agnostic and finds variants in less than two hours on a standard server.

In further embodiments, an artificial neural network can be used as a discriminator as a substitute to expert review on clinically significant genomics variants. Many rare diseases and cancers are fundamentally diseases of the genome. Genome sequencing has become one of the most important tools in clinical practice for rare disease diagnosis and targeted cancer therapy. However, variant interpretation remains a significant bottleneck due to lack of sufficient automation and because it may take a specialist several hours of work per patient. On average, one-fifth of this time is spent on visually confirming the authenticity of the candidate variants. Embodiments of the present disclosure have been experimentally verified by the present inventors to run in less than one minute to automatically review ten thousand variants, and approximately 30 minutes to review all variants in a typical whole-genome sequencing sample. Among the false positive singletons identified by GATK HaplotypeCaller, UnifiedGenotyper and 16GT in the HG005 GIAB sample, 79.7% were determined to be rejected by the present embodiments. Worked on the Variants with Unknown Significance (VUS), the present embodiments were able to mark most of the false positive variants for manual review and most of the true positive variants as no need for review.

The dramatic reduction in the cost of whole genome, exome and amplicon sequencing has allowed these technologies to be increasingly accessible for genetic testing, opening the door to broad applications in Mendelian disorders, cancer diagnosis and personalized medicine. However, sequencing data include both systematic and random errors that hinder any of the current variant identification algorithms from working optimally. Using most approaches, typically 1-3% of the candidate variants are false positives with Illumina sequencing. With the help of a genome browser such as IGV, or web applications such as VIPER, a specialist can visually inspect a graphical layout of the read alignments to assess supporting and contradicting evidence to make an arbitration. Though necessary, this is a tedious and fallible procedure because of three major drawbacks: 1) it is time-consuming and empirical studies report it requires about one minute per variant, sometimes summing up to a few hours per patient; 2) it is tedious, not infallible, and even experienced genetic-specialists might draw different conclusions for a candidate variant with limited or contradicting evidence; and 3) there is no agreed standard between genetic-specialists to judge various types of variants, including SNPs (Single Nucleotide Polymorphisms) and Indels. A specialist might be more stringent on SNPs because there are more clinical assertions and fewer candidate SNPs will be less likely to get contradicting medical conclusions, whereas another specialist might be more demanding on indels because they are rarer and harder to be identified.

The present embodiments advantageously provide an efficient, accurate and consistent computational method that automates assessing the candidate variants. Additionally, the validation method of the present embodiments is orthogonal, i.e., independent of the algorithms used to identify the candidate variants. Additionally, the validation method of the present embodiments is able to capture the complex non-linear relationship between read alignments and the authenticity of a variant from a limited amount of labeled training data. Variant validation is a task with a different nature from variant filtration. The present embodiments are able to indicate the need of a variant being manually reviewed, as opposed to a hard filter that removes a variant from consideration. In some cases, failing to flag a false positive variant for review is less favorable than flagging a true variant for manual review, i.e., as a validation method, the precision must be maximized, and false positives must be minimized. Consequently, instead of using hand-coded models or rule-based learning, the present embodiments employ a more powerful and agnostic machine learning approach such as an artificial neural network.

Embodiments of the system 100 can be used as an orthogonal approach for validating of candidate variants from a separate variant caller. In these embodiments, the system 100 uses the discriminator module 156 to provide fast and accurate validation of candidate variants from the separate variant caller. The separate variant caller can include; for example, GATK HaplotypeCaller, Freebayes, or the like. The discriminator module 156 can automatically determine whether the evidence supports or contradicts sequencing read alignments output by the separate variant caller. Using the CNN described herein, a probability of each possible option for multiple categories can be generated by the CNN. The categories include 1) variant type, 2) alternative allele, 3) zygosity, and 4) indel-length. A candidate variant output by the variant caller can then be compared to a prediction on each category. The discriminator module 156 will agree with a variant if all categories are matched but will reject and provide possible corrections if any category is unmatched. The CNN model for the discriminator can be trained using known variants having known output variables, as described herein. The known variants can be sourced from, for example, sequencing libraries such as those prepared by either a polymerase chain reaction (PCR) or the PCR-free protocol. With a trained model, the discriminator module 156 accepts, from the separate variant caller, an input with candidate SNPs and Indels (for example, as a Variant Call Format (VCF) file) and an input with read alignments (for example, as a Binary Alignment/Map (BAM) file). The discriminator module 156 outputs a judgment and a quality score on how confident the judgment was made for each candidate variant. In an example, the discriminator module 156 can use Tensorflow, in some cases, that has been tuned to maximize its speed.

Figure 7:
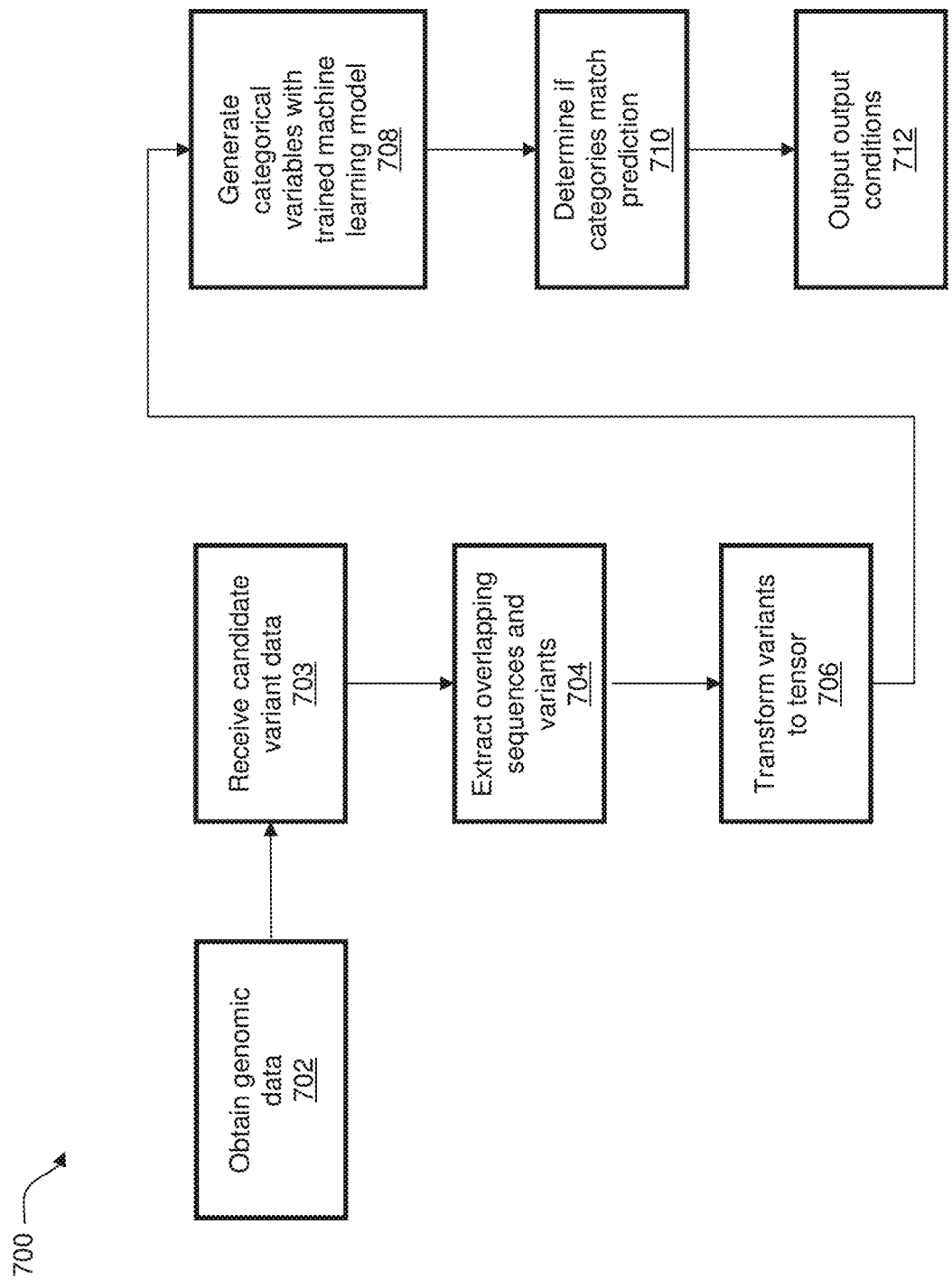
FIG. 7 is a flow chart of a method of discriminating genomic variants, in accordance with an embodiment.

Turning to FIG. 7, a flowchart for a method of discriminating genomic variants, according to an embodiment, is shown.

At block 702, the input module 150 obtains genomic data, for example, from the network interface 110, the input interface 106, or the database 116.

At block 703, the input module 150 receives candidate variant data that is outputted from a separate variant caller. The variant data is associated with the genomic data and includes candidate variants and properties of the candidate variants including all, or a subset of, categories including: 1) variant type, 2) alternative allele, 3) zygosity, and 4) indel-length.

At block 704, the input module 150 extracts overlapping sequencing read alignments from the genomic data and determines variants where the read alignments differ.

At block 706, the input module 150 transforms the overlapping sequencing read alignments and associated variants into a multi-dimensional tensor. In a particular case, a shape of the multi-dimensional tensor can have three dimensions; a first dimension corresponding to a position of a variant, a second dimension corresponding to a count of a base (A, C, G, or T) on a sequencing read, and a third dimension corresponding to different ways of counting bases.

At block 708, the machine learning module 152 passes the multi-dimensional tensor through a trained machine learning architecture to generate probabilities for outcomes in each category of output variables by minimizing a cost function iterated over each variant. The categorical output variables include alternate base at a single-nucleotide polymorphism, zygosity of a variant, variant type, and length of an indel. The machine learning architecture is trained using a genomic dataset with previously identified variants (i.e., truth variants). The trained machine learning architecture can have the same structure as the other embodiments described herein.

At block 710, the discriminator module 156 compares each of one or more candidate variants against the machine learning model's prediction on each category for that candidate variant. The discriminator module 156 will output a positive condition for a variant if all categories are matched and will output a negative condition if any category is unmatched. In some embodiments, the discriminator module 156 also outputs the output condition and a quality score on how confident the judgment was made for each candidate variant. In a particular case, the quality score can be determined using a Phred-scale of the distance between the best prediction and the second-best prediction of the machine learning model. The best prediction being an average of the best probability of the four categories. The second-best prediction being an average of the second-best probability of the four categories.

At block 712, the output module 154 outputs the output condition, and in some cases, the quality score. In some cases, the output module 154 also output the categorical output variables outputted by the trained machine learning architecture.

Figure 8:
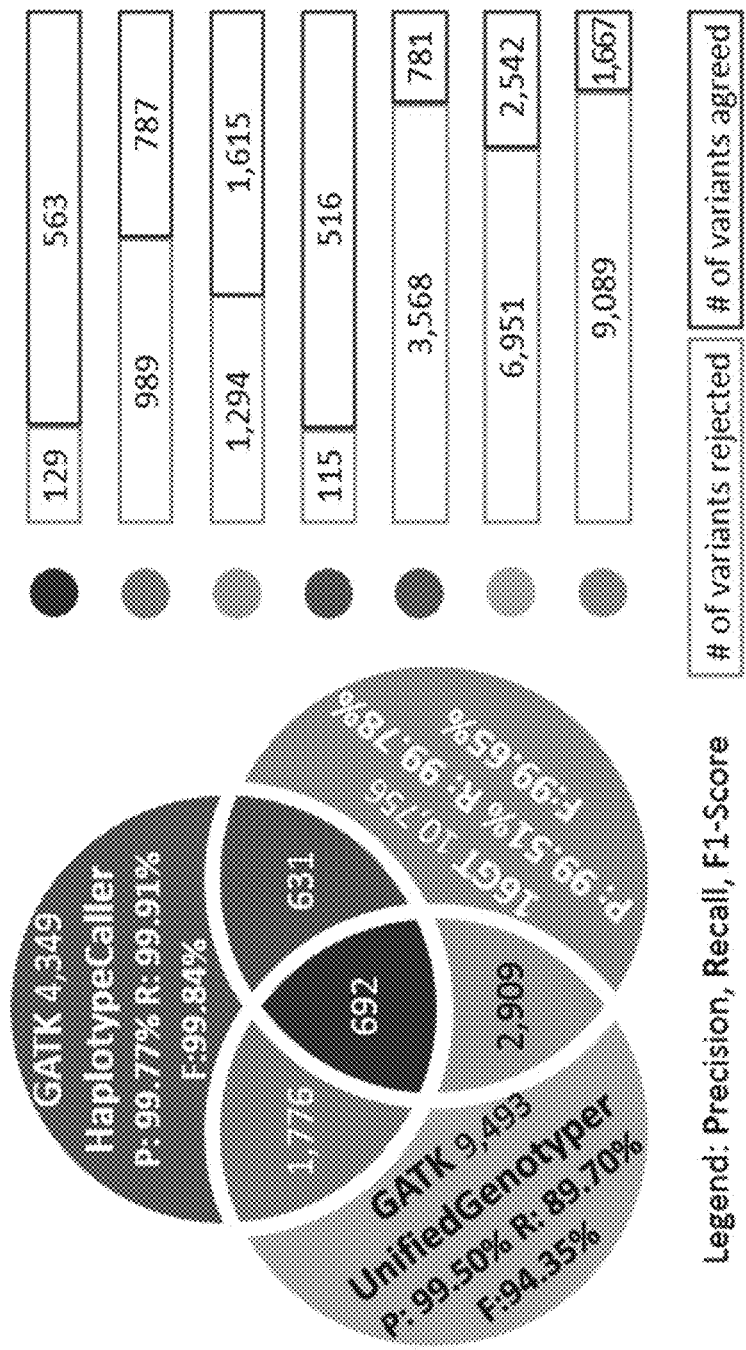
FIG. 8 illustrates an example Venn diagram of a variant set called by the three callers, in accordance with the system of FIG. 1.

In example experiments, the present inventors verified the ability of embodiments of the system 100 to validate candidate variants. The example experiments used four deeply Illumina sequenced genomes (HG001, HG002, HG003, and HG004) with 13.5 M known truth variants from the Genome In A Bottle (GIAB) database. Using the truth variants, the neural network was trained to recognize how the truth variants are different from another 20 M non-variants that were randomly sampled from the four genomes. For benchmarking and identifying the false positive variant calls, the known truth variants in HG005 were used; which were not included in the model training. A false positive variant is defined as a variant called by a variant caller but cannot be found in the HG005 GIAB truth dataset and will be used for the subsequent analysis. It was hypothesized that the false positive variants that are supported by only one variant caller, but not the other variant callers are very likely to be erroneous and should be marked for manual review (i.e., rejected) by the system 100. Thus, variants were called using three different variant callers with different calculation models, including GATK HaplotypeCaller (HC), GATK UnifiedGenotyper (UG) and 16GT. FIG. 8 illustrates a Venn diagram of a variant set called by the three callers, which comprise seven different types of variants: 1) three types of singleton variants that have support from only one caller, 2) three types of doubleton variants that have support from two of the three callers, and 3) one type of tripleton variant that is supported by all three callers. Empirically, doubleton and especially tripleton variants are relatively less likely to be real false positives and should be less likely to be rejected by the system 100. Conversely, singletons called by only one caller are more likely to be genuine false positive and should be more likely to be rejected by the system 100.

The results of the example experiments are shown in FIG. 8, showing the variant calling results of GATK HaplotypeCaller, GATK UnifiedGenotyper, and 16GT. The Venn diagram shows 1) the precision rate (P), recall rate (R) and f1-score (F) of each variant caller on all variants of the entire HG005 genome, and 2) the number of false positive variants produced by each variant caller. The bars graphs shows the number of false positive variants rejected or agreed by the system 100. The bar length is proportionate to the total number of false positive variants in that type. Only 18.64% of the tripleton variants were rejected while 79.70% of the singletons were rejected by the system 100. Those doubletons have an intermediate 45.11% rejected by the system 100. In the true positive variants, only 1,879/3,232,539 (0.058%) in HC, 43/2,902,052 (0.0014%) in UG, and 124/3,228,537 (0.0038%) in 16GT were rejected. By deducting the rejected variants from both the number of true positives and true negatives, the precision increased from 99.77% to 99.92% for HC, 99.50% to 99.58% for UG and 99.51% to 99.84% for 16GT.

In other example experiments, the present inventors verified the ability of embodiments of the system 100 to validate candidate variants. Instead of fully automatizing and thus removing manual review, which may not be allowed in a stringent clinical context that emphasizes accountability, the system 100 can be used to help medical professionals prioritize which variants they should likely invest efforts in further investigation and lab validation. In practice, those variants categorized as "Pathogenic" or "Likely Pathogenic" are rare and should be given priority, thus all these variants are preferred to be manually reviewed. "Benign", and most of the time together with the "Likely Benign" category, suggest variants without much value in clinical diagnosis and therapy, thus likely not requiring manual review. The other category, named Variant of Unknown Significance, or VUS, contains variants that are potentially impactful, and requires doctors to sort through them. With some approaches, the number of VUS can typically be tens to even hundreds of time larger than the sum of other categories. Thus, the present embodiments can benefit the clinical practitioners because it has been found to significantly decrease the number VUS to be manually reviewed.

In the example experiments, to assess the intended function, GATK HaplotypeCaller was run on the HG002 sample. In total about 5 M variants were called. Then the variants were annotated using SeattleSeq version 151 (with dbSNP v151). Variants were extracted that were 1) not in dbSNP (RSID tag equals to 0), and 2) are in a human gene (GL tag not empty). Then, the system 100 was run on the extracted variants with a model trained on four samples including HG001, HG003, HG004, and HG005, and annotated the variants as either true positive (TP) or false positive (FP) against the HG002 GIAB truth dataset. The system 100 performed substantially well, and the results are shown in TABLE 5.

TABLE 5

|    |       | PASS  |       | CHECK |       |
|----|-------|-------|-------|-------|-------|
|    |       | #     | %     | #     | %     |
| TP | SNP   | 4,837 | 99.7% | 14    | 0.3%  |
|    | Indel | 7,126 | 74.5% | 2,434 | 25.5% |
| FP | SNP   | 117   | 46.6% | 134   | 53.4% |
|    | Indel | 41    | 21.7% | 148   | 78.3% |

In the example experiments, for SNPs, 53.4% of the FPs were flagged for manual review, while only 0.3% of the TPs were flagged. For Indels, 78.3% of the FPs were flagged for manual review, while only 25.5% of the TPs were flagged. A higher rate of TP Indels were flagged for manual review because longer Indels are usually more error-prone and can lead to more severe clinical consequences than SNPs, thus it was decided to require all Indels to be manually reviewed. As shown, the example experiments illustrate the system 100 has significantly more FP variants marked for manual review than TP variants, verifying the system's 100 effectiveness.

Advantageously, the present embodiments can relieve users from a heavy manual review workload without compromising accuracy. In some cases, instead of taking over the review of all variants, the system 100 can be configured to review only 1) SNPs with a single alternative allele, and 2) Indels ≤4 bp. The system 100 can also output a quality score ranging from 0 to 999 to indicate the confidence of a judgment. Advantageously, the system 100 can require less than a gigabyte of memory and less than a minute on one CPU core to review ten thousand variants, thus can be easily integrated into existing manual review workflows with minimal computational burden. Using 24 CPU cores, the system 100 was able to review all five million whole genome sequencing variants of the HG002 sample in 30 minutes. Advantageously, the present embodiments greatly reduce the workload on reviewing variants, and thus can greatly increase the productivity of genetic-specialists in clinical practice.

Although the invention has been described with reference to certain specific embodiments, various modifications thereof will be apparent to those skilled in the art without departing from the spirit and scope of the invention as outlined in the claims appended hereto.

The invention claimed is:

1. A computer-implemented method for variant calling in single molecule sequencing from a genomic dataset using a convolutional deep neural network, the method comprising causing one or more processors of the computer to perform steps of:

obtaining variants of the genomic dataset;
transforming properties of each of the variants into a multi-dimensional tensor;
passing the multi-dimensional tensor through a convolutional deep neural network trained to predict categorical output variables, the convolutional deep neural network minimizing a cost function iterated over each variant, the convolutional deep neural network trained using a training genomic dataset comprising previously identified variants, the convolutional neural network comprising:
an input layer;
a plurality of pooled convolutional layers connected sequentially after the input layer, each pooled convolutional layer taking an input, applying at least one convolutional operation to the input, and applying a pooling operation to the output of the convolutional operation; and
at least two fully-connected layers connected sequentially after the last of the pooled convolutional layers, the at least two fully-connected layers comprising a second fully-connected layer connected sequentially after a first fully-connected layer; and
outputting the predicted categorical output variables;
wherein,
for each variant, the categorical output variables comprise:
a first categorical output variable comprising an alternate base at a single-nucleotide polymorphism;
a second categorical output variable comprising zygosity;
a third categorical output variable comprising type; and
a fourth categorical output variable comprising length of an insertion or deletion of bases;
the first categorical output variable is selected from a group comprising adenine (A), cytosine (C), guanine (G), and thymine (T);
the second categorical output variable is selected from a group comprising Homozygote and Heterozygote;
the third categorical output variable is selected from a group comprising Reference, SNP, Insertion, and Deletion;
the fourth categorical output variable is selected from a group comprising 0, 1, 2, 3, 4, and greater than 4;
the first categorical output variable is output from the first fully-connected layer, and the second categorical output variable, the third categorical output variable, and the fourth categorical output variable are outputted from the second fully-connected layer; and
the plurality of pooled convolutional layers comprises three pooled convolutional layers.

2. The method of claim 1, wherein the first fully-connected layer comprises a regression analysis using a sigmoid activation function, and the second fully-connected layer comprises a softmax classification analysis.

3. The method of claim 1, wherein the plurality of pooled convolutional layers comprises exactly three pooled convolutional layers.

4. A computer-implemented method for variant calling in single molecule sequencing from a genomic dataset using a convolutional deep neural network, the method comprising causing one or more processors of the computer to perform steps of:
obtaining variants of the genomic dataset;
transforming properties of each of the variants into a multi-dimensional tensor;
passing the multi-dimensional tensor through a trained convolutional deep neural network to predict categorical output variables, the convolutional deep neural network minimizing a cost function iterated over each variant, the convolutional deep neural network trained using a training genomic dataset comprising previously identified variants, the convolutional neural network comprising:
an input layer;
a plurality of pooled convolutional layers connected sequentially after the input layer, each pooled convolutional layer taking an input, applying at least one convolutional operation to the input, and applying a pooling operation to the output of the convolutional operation; and
at least two fully-connected layers connected sequentially after the last of the pooled convolutional layers, the at least two fully-connected layers comprising a second fully-connected layer connected sequentially after a first fully-connected layer; and
outputting the predicted categorical output variables;
wherein,
for each variant, the categorical output variables comprise:
a first categorical output variable comprising an alternate base at a single-nucleotide polymorphism;
a second categorical output variable comprising zygosity;
a third categorical output variable comprising type; and
a fourth categorical output variable comprising length of an insertion or deletion of bases; and
the multi-dimensional tensor comprises a first dimension corresponding to a position of the variant in addition to flanking base pairs, a second dimension corresponding to a count of a base on a sequencing read, and a third dimension corresponding to a number of techniques for counting bases.

5. The method of claim 4, wherein the first dimension comprises sixteen flanking base pairs on both sides of the variant for a total dimension of thirty-three, the second dimension comprises adenine (A), cytosine (C), guanine (G), and thymine (T) for a total dimension of four, and the third dimension comprises four techniques for counting bases for a total dimension of four.

6. The method of claim 5, wherein the four techniques comprise a first technique for encoding a reference sequence and a number of reads supporting reference alleles, and the second technique encodes inserted sequences, the third technique encodes deleted base-pairs, and the fourth technique encodes alternative alleles.

7. A system for variant calling in single molecule sequencing from a genomic dataset using a convolutional deep neural network, the system comprising one or more processors and one or more non-transitory computer storage media, the one or more non-transitory computer storage media causing the one or more processors to execute:
an input module to obtain variants of the genomic dataset and transform properties of each of the variants into a multi-dimensional tensor;
a machine learning module to pass the multi-dimensional tensor through a convolutional deep neural network trained to predict categorical output variables, the convolutional deep neural network minimizing a cost function iterated over each variant, the convolutional deep neural network trained using a training genomic dataset comprising previously identified variants, the convolutional neural network comprising:
an input layer;
a plurality of pooled convolutional layers connected sequentially after the input layer, each pooled convolutional layer taking an input, applying at least one convolutional operation to the input, and applying a pooling operation to the output of the convolutional operation; and at least two fully-connected layers connected sequentially after the last of the pooled convolutional layers, the at least two fully-connected layers comprising a second fully-connected layer connected sequentially after a first fully-connected layer; and an output module to output the predicted categorical output variables;

wherein, for each variant, the categorical output variables comprise:

a first categorical output variable comprising an alternate base at a single-nucleotide polymorphism;

a second categorical output variable comprising zygosity;

a third categorical output variable comprising type; and a fourth categorical output variable comprising length of an insertion or deletion of bases;

the first categorical output variable is selected from a group comprising adenine (A), cytosine (C), guanine (G), and thymine (T);

the second categorical output variable is selected from a group comprising Homozygote and Heterozygote;

the third categorical output variable is selected from a group comprising Reference, SNP, Insertion, and Deletion;

the fourth categorical output variable is selected from a group comprising 0, 1, 2, 3, 4, and greater than 4;

the first categorical output variable is output from the first fully-connected layer, and the second categorical output variable, the third categorical output variable, and the fourth categorical output variable are outputted from the second fully-connected layer; and the plurality of pooled convolutional layers comprises three pooled convolutional layers.

8. The system of claim 7, wherein the first fully-connected layer comprises a regression analysis using a sigmoid activation function, and the second fully-connected layer comprises a softmax classification analysis.

9. The system of claim 7, wherein the plurality of pooled convolutional layers comprises exactly three pooled convolutional layers.

* * * * *

SEQUENCE LISTING

<160> NUMBER OF SEQ ID NOS: 9

<210> SEQ ID NO 1
<211> LENGTH: 48
<212> TYPE: DNA
<213> ORGANISM: Unknown
<220> FEATURE:
<223> OTHER INFORMATION: Reference Sequence

<400> SEQUENCE: 1
acgtacggtt acacaaaccc gtttgcacgt acgtaaaccg ttgtgacg        48

<210> SEQ ID NO 2
<211> LENGTH: 19
<212> TYPE: DNA
<213> ORGANISM: Unknown
<220> FEATURE:
<223> OTHER INFORMATION: Layout Sequence

<400> SEQUENCE: 2
ttacacaatc ccgttcgca        19

<210> SEQ ID NO 3
<211> LENGTH: 19
<212> TYPE: DNA
<213> ORGANISM: Unknown
<220> FEATURE:
<223> OTHER INFORMATION: Layout Sequence

<400> SEQUENCE: 3
tacacaatcc cgttcgcac        19

<210> SEQ ID NO 4

```
<211> LENGTH: 19
<212> TYPE: DNA
<213> ORGANISM: Unknown
<220> FEATURE:
<223> OTHER INFORMATION: Layout Sequence

<400> SEQUENCE: 4
acacaatccc gttcgcacg                                            19

<210> SEQ ID NO 5
<211> LENGTH: 19
<212> TYPE: DNA
<213> ORGANISM: Unknown
<220> FEATURE:
<223> OTHER INFORMATION: Layout Sequence

<400> SEQUENCE: 5
cacaatcccg ttcgcacgt                                            19

<210> SEQ ID NO 6
<211> LENGTH: 19
<212> TYPE: DNA
<213> ORGANISM: Unknown
<220> FEATURE:
<223> OTHER INFORMATION: Layout Sequence

<400> SEQUENCE: 6
caatcccgtt cgcacgtac                                            19

<210> SEQ ID NO 7
<211> LENGTH: 19
<212> TYPE: DNA
<213> ORGANISM: Unknown
<220> FEATURE:
<223> OTHER INFORMATION: Layout Sequence

<400> SEQUENCE: 7
aatcccgttc gcacgtacg                                            19

<210> SEQ ID NO 8
<211> LENGTH: 19
<212> TYPE: DNA
<213> ORGANISM: Unknown
<220> FEATURE:
<223> OTHER INFORMATION: Layout Sequence

<400> SEQUENCE: 8
atcccgttcg cacgtacgt                                            19

<210> SEQ ID NO 9
<211> LENGTH: 26
<212> TYPE: DNA
<213> ORGANISM: Unknown
<220> FEATURE:
<223> OTHER INFORMATION: Consensus Sequence

<400> SEQUENCE: 9
ttacacaatc ccgttcgcac gtacgt                                    26
```